(12) United States Patent
Halpern et al.

(10) Patent No.: US 8,725,422 B2
(45) Date of Patent: May 13, 2014

(54) METHODS FOR ESTIMATING GENOME-WIDE COPY NUMBER VARIATIONS

(75) Inventors: Aaron Halpern, San Carlos, CA (US); Krishna Pant, San Jose, CA (US)

(73) Assignee: Complete Genomics, Inc., Mountain View, CA (US)

( * ) Notice: Subject to any disclaimer, the term of this patent is extended or adjusted under 35 U.S.C. 154(b) by 0 days.

(21) Appl. No.: 13/270,989

(22) Filed: Oct. 11, 2011

(65) Prior Publication Data

US 2012/0095697 A1     Apr. 19, 2012

Related U.S. Application Data

(60) Provisional application No. 61/392,567, filed on Oct. 13, 2010, provisional application No. 61/503,327, filed on Jun. 30, 2011.

(51) Int. Cl.
    G01N 33/48    (2006.01)
    G06F 19/00    (2011.01)
    G06F 19/18    (2011.01)

(52) U.S. Cl.
    CPC ..................................... G06F 19/18 (2013.01)
    USPC .............................................. 702/19; 702/20

(58) Field of Classification Search
    CPC ..................................................... G06F 19/18
    See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis et al. |
| 4,800,159 A | 1/1989 | Mullis et al. |
| 4,883,750 A | 11/1989 | Whiteley et al. |
| 4,965,188 A | 10/1990 | Mullis et al. |
| 5,210,015 A | 5/1993 | Gelfand et al. |
| 5,399,491 A | 3/1995 | Kacian et al. |
| 5,476,930 A | 12/1995 | Letsinger et al. |
| 5,593,826 A | 1/1997 | Fung et al. |
| 5,795,782 A | 8/1998 | Church et al. |
| 5,854,033 A | 12/1998 | Lizardi |
| 5,871,921 A | 2/1999 | Landegren et al. |
| 6,015,714 A | 1/2000 | Baldarelli et al. |
| 6,174,670 B1 | 1/2001 | Wittwer et al. |
| 6,210,891 B1 | 4/2001 | Nyren et al. |
| 6,287,824 B1 | 9/2001 | Lizardi |
| 6,306,597 B1 | 10/2001 | Macevicz |
| 6,309,824 B1 | 10/2001 | Drmanac |
| 6,401,267 B1 | 6/2002 | Drmanac |
| 6,627,067 B1 | 9/2003 | Branton et al. |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,911,345 B2 | 6/2005 | Quake et al. |
| 7,238,485 B2 | 7/2007 | Akeson et al. |
| 7,258,838 B2 | 8/2007 | Li et al. |
| 7,329,496 B2 | 2/2008 | Dower et al. |
| 7,709,197 B2 | 5/2010 | Drmanac |
| 7,897,344 B2 | 3/2011 | Dahl et al. |
| 7,901,890 B2 | 3/2011 | Dahl et al. |
| 7,906,285 B2 | 3/2011 | Drmanac |
| 7,910,302 B2 | 3/2011 | Drmanac et al. |
| 7,910,304 B2 | 3/2011 | Drmanac |
| 7,910,354 B2 | 3/2011 | Drmanac et al. |
| 7,960,104 B2 | 6/2011 | Drmanac et al. |
| 8,105,771 B2 | 1/2012 | Drmanac |
| 8,133,719 B2 | 3/2012 | Drmanac et al. |
| 8,278,039 B2 | 10/2012 | Drmanac |
| 8,298,768 B2 | 10/2012 | Drmanac et al. |
| 8,415,099 B2 | 4/2013 | Drmanac et al. |
| 8,440,397 B2 | 5/2013 | Drmanac et al. |
| 8,445,194 B2 | 5/2013 | Drmanac et al. |
| 8,445,196 B2 | 5/2013 | Drmanac et al. |
| 8,445,197 B2 | 5/2013 | Drmanac et al. |
| 2006/0003171 A1 | 1/2006 | Igawa et al. |
| 2006/0024711 A1 | 2/2006 | Lapidus et al. |
| 2007/0168197 A1 | 7/2007 | Vasilache |
| 2008/0171331 A1 | 7/2008 | Drmanac |
| 2008/0182257 A1 | 7/2008 | Bastian et al. |
| 2008/0213771 A1 | 9/2008 | Drmanac |
| 2008/0221832 A1 | 9/2008 | Drmanac |

(Continued)

FOREIGN PATENT DOCUMENTS

WO    WO-2006/073504 A2    7/2006
WO    WO-2006/138257 A2    12/2006

(Continued)

OTHER PUBLICATIONS

Bengtsson et al. "Estimation and assessment of raw copy numbers at the single locus level," Bioinformatics, vol. 24 (2008) pp. 759-767.*
Carnevali et al., "Computation Techniques for Human Genome Resequencing Using Mated Gapped Reads," *Journal of Computational Biology*, Dec. 16, 2011, 19(3):279-292.
International Search Report and Written Opinion dated Sep. 17, 2013 from International Patent Application No. PCT/US2013/039777, 10 pages.
Drmanac et al., "Human Genome Sequencing Using Unchained Base Reads on Self-Assembling DNA Nanaoarrays," Jan. 1, 2010, *Science* 327:78-81.
Margulies et al., "Genome sequencing in microfabricated high-density picolitre reactors," Sep. 2005, *Nature* 437:376-380 (Errata p. 441:120 from Mar. 2006 attached).
Ronaghi et al., "Real-Time DNA Sequencing Using Detection of Pyrophosphate Release," 1996, *Anal. Biochem.* 242:84-89.
Mullikin, et al, "Whole-Exome Sequencing: Technical Details", accessed at http://www.genome.gov/pages/research/dir/dimewsfeatures/nextgen101/mullikin_wholeexomesequencing.pdf on Sep. 3, 2013.

*Primary Examiner* — Anna Skibinsky
(74) *Attorney, Agent, or Firm* — Duane Morris LLP

(57) ABSTRACT

Methods for determining the copy number of a genomic region at a detection position of a target sequence in a sample are disclosed. Genomic regions of a target sequence in a sample are sequenced and measurement data for sequence coverage is obtained. Sequence coverage bias is corrected and may be normalized against a baseline sample. Hidden Markov Model (HMM) segmentation, scoring, and output are performed, and in some embodiments population-based no-calling and identification of low-confidence regions may also be performed. A total copy number value and region-specific copy number value for a plurality of regions are then estimated.

27 Claims, 3 Drawing Sheets

(56) References Cited

U.S. PATENT DOCUMENTS

| | | |
|---|---|---|
| 2009/0005252 A1 | 1/2009 | Drmanac et al. |
| 2009/0011943 A1 | 1/2009 | Drmanac et al. |
| 2009/0029477 A1 | 1/2009 | Meller et al. |
| 2009/0075343 A1 | 3/2009 | Sparks et al. |
| 2009/0098547 A1 | 4/2009 | Ghosh |
| 2009/0105961 A1 | 4/2009 | Drmanac |
| 2009/0111115 A1 | 4/2009 | Drmanac et al. |
| 2009/0111705 A1 | 4/2009 | Sparks et al. |
| 2009/0111706 A1 | 4/2009 | Sparks et al. |
| 2009/0118488 A1 | 5/2009 | Drmanac et al. |
| 2009/0176234 A1 | 7/2009 | Drmanac et al. |
| 2009/0264299 A1 | 10/2009 | Drmanac et al. |
| 2010/0227768 A1 | 9/2010 | Wigler et al. |
| 2010/0286925 A1 | 11/2010 | Halpern et al. |
| 2010/0287165 A1 | 11/2010 | Halpern et al. |
| 2011/0004413 A1 | 1/2011 | Carnevali et al. |
| 2011/0015864 A1 | 1/2011 | Halpern et al. |
| 2012/0095697 A1 | 4/2012 | Halpern et al. |

FOREIGN PATENT DOCUMENTS

| | | |
|---|---|---|
| WO | WO-2006/138284 A2 | 12/2006 |
| WO | WO-2007/044245 A2 | 4/2007 |
| WO | WO-2007/120208 A2 | 10/2007 |
| WO | WO-2007/133831 A2 | 11/2007 |
| WO | WO-2008/058282 A2 | 5/2008 |
| WO | WO-2008/070352 A2 | 6/2008 |
| WO | WO-2008/070375 A2 | 6/2008 |

* cited by examiner

METHODS FOR ESTIMATING GENOME-WIDE COPY NUMBER VARIATIONS

PRIORITY

This application claims benefit and priority of U.S. Provisional Application Ser. No. 61/392,567, filed on Oct. 13, 2010, the entire contents of which are hereby incorporated by reference as if fully set forth herein; this application also claims the benefit and priority of U.S. Provisional Application Ser. No. 61/503,327, filed on Jun. 30, 2011, the entire content of which is hereby incorporated by reference as if fully set forth herein.

BACKGROUND

Genomic abnormalities are often associated with various genetic disorders, degenerative diseases, and cancer. For example, the deletion or multiplication of copies of genes and the deletion or amplifications of genomic fragments or specific regions are common occurrences in cancer. For instance, alterations in proto-oncogenes and tumor-suppressor genes, respectively, are frequently characteristic of tumorigenesis. The identification and cloning of specific genomic regions associated with cancer and various genetic disorder is therefore of interest both to the study of tumorigenesis and in developing better means of diagnosis and prognosis.

Identification of polynucleotides that correspond to copy number alterations in cancerous, pre-cancerous, or low metastatic potential cells relative to normal cells of the same tissue type, provides the basis for diagnostic tools, facilitates drug discovery by providing for targets for candidate agents, and further serves to identify therapeutic targets for cancer therapies that are more tailored for the type of cancer to be treated.

In diagnostic genome sequencing, the computational complexity involved in sequence analysis of three billion base pairs in the human genome is further compounded by the accuracy requirements of clinical diagnostics such that 60 billion or more sequence data points must be analyzed to provide one accurate genome sequence. This complexity was dealt with in early sequencing methods by generating sequence data from thousands of isolated, very long fragments of DNA, thereby preserving the contextual integrity of the sequence information and reducing the redundant testing required for accurate data. However, this approach, used to generate the first complete human genome, cost hundreds of millions of dollars per genome due to the up-front complexity of preparing the genome fragments and the relative high cost of many individual biochemical tests.

In addition, contextual information in the genome is compounded by the presence of two distinct copies of the genome in each human cell such that accurate clinical analysis and diagnosis requires the ability to distinguish DNA sequence as a function of genome copy. Thus, a major challenge is to distinguish sequence differences between the two unique copies of the three billion DNA bases interspersed with millions of inherited single nucleotide polymorphisms (SNPs), hundreds of thousands of short insertions and deletions and hundreds of spontaneous mutations.

Some approaches have been developed that aid in the identification of copy number variants ("CNV") within a complete DNA sequence, and to aid in the confidence of the identification based on comparison of the sequence with reference sequences or multiple different copies of the sequence. In these approaches identification of copy number and its validation is based on different sets of samples, and the data used in such approaches is relatively error-prone and known to harbor certain artifactual biases.

SUMMARY

The present invention provides methods for determining the copy number of a genomic region at a detection position of a target polynucleotide sequence in a sample, said method comprising: obtaining measurement data for the sequence coverage for said sample; correcting the measurement data for sequence coverage bias; wherein the sequence coverage bias correction comprises performing ploidy-aware baseline correction; and estimating a total copy number value and region-specific copy number value for a plurality of genomic regions. In one embodiment, the method comprises performing Hidden Markov Model (HMM) segmentation, scoring, and output. In another embodiment, the method comprises performing population-based no-calling and identification of low-confidence regions.

In one aspect, the method further comprises normalization of sequence coverage by comparison to a baseline sample.

In one aspect, the method further comprises the determination of the sequence coverage by measuring sequence coverage depth at every position of the genome of the sample.

In one aspect, the method further comprises correction of the sequence bias by calculating window-averaged coverage.

In one aspect, the method further comprises adjustments to account for GC bias in the library construction and sequencing process.

In a further embodiment, the method further comprises performing adjustments based on additional weighting factor associated with individual mappings to compensate for bias.

In one aspect, the method further comprises steps performed by a sequencing machine, said steps comprising: a) providing a plurality of amplicons, wherein: i) each amplicon comprises multiple copies of a fragment of the target nucleic acid, ii) each amplicon comprises a plurality of interspersed adaptors at predetermined sites within the fragment, each adaptor comprising at least one anchor probe hybridization site, and iii) said plurality of amplicons comprise fragments that substantially cover the target nucleic acid; b) providing a random array of said amplicons fixed to a surface at a density such that at least a majority of said amplicons are optically resolvable; c) hybridizing one or more anchor probes to said random array; d) hybridizing one or more sequencing probes to said random array to form perfectly matched duplexes between said one or more sequencing probes and fragments of target nucleic acid; e) ligating the anchor probes to the sequencing probes; and f) identifying at least one nucleotide adjacent to at least one interspersed adaptor; and g) repeating steps (c) through (f) until a nucleotide sequence of said target nucleic acid is identified.

In one aspect, the method further comprises determining the measurement data by performing steps comprising: a) determining reads representing the sequences of a plurality of approximately random fragments of the genome in a sample, wherein said plurality provides a sampling of the genome of the sample whereby on average a base position of the genome is sampled one or more times; b) obtaining mapping data for said reads by mapping said reads to the reference genome, or by mapping said reads to an assembled sequence (e.g., such as the assembled sequence of the sample itself or the assembled sequence of a related baseline sample); and c) obtaining coverage data by measuring the intensity of said reads along the reference genome or along the assembled sequence, wherein the measurement data comprises the mapping data and the coverage data.

In a further embodiment, the method further comprises generation of an initial model that estimates the number of states and their means based on the overall coverage distribution.

In a further embodiment, the method further comprises optimization of an initial model by sequentially adding states to the model and then sequentially removing states from the model, or combination thereof.

In a further embodiment, the normalization further comprises the determination of normalized corrected coverage.

In a further embodiment, the method further comprises determining sequence coverage by segmental duplications and obtaining confidence measurements to fractionally attribute the mapping to each detection location.

In one aspect, the method comprises HMM calculations performed to determine a ploidy number at each detection position.

In a further embodiment, the method further comprises generating a plurality of states of a Hidden Markov Model (HMM) that correspond to respective copy numbers, wherein if the sample is a normal sample, then performing HMM segmentation, scoring, and output, including: initializing a mean of an emission distribution of the HMM for each state with copy number N greater than zero to N/2 multiplied by the median of the coverage in a portion of the sample expected to be diploid; and initializing the mean of the emission distribution for the state with copy number 0 to a positive value smaller than that used for the state with copy number 1.

In a further embodiment, the method further comprises generating plural states of an HMM that correspond to respective copy numbers, wherein if the sample is a tumor sample, then performing HMM segmentation, scoring, and output, including: estimating the number of states and a mean of each state based on a distribution of the coverage to generate an initial model for the HMM; optimizing the initial model by modifying the number of states in the model as well as optimizing the parameters of each state; and modifying the number of states in the model by sequentially adding states to the model and then sequentially removing states, or a combination thereof.

In a further embodiment, the method further comprises adjusting the initial model that comprises: a) adding a new state between a pair of states if adding said new state improves a likelihood associated with the HMM beyond a first predetermined threshold; b) repeating step (a) recursively between each pair of states until no more additions are possible; c) removing a state from the HMM if removal of said state does not decrease the likelihood beyond a second predetermined threshold; and d) repeating step (c) iteratively for all the states.

A further embodiment comprises a computer-readable non-transitory storage medium having instructions stored thereon for determining the copy number of a genomic region at a detection position of a target polynucleotide sequence in a sample, the instructions when executed by a computer processor causing the processor to perform the operations of: obtaining measurement data for the sequence coverage for said sample using data generated from mate-pair mappings; correcting the measurement data for sequence coverage bias, wherein correcting the measurement data comprises performing ploidy-aware baseline correction; and based at least on the corrected measurement data, estimating a total copy number value and region-specific copy number value for each of a plurality of genomic regions.

A further embodiment comprises a computer-readable non-transitory storage medium having instructions tangibly embodied thereon, the instructions when executed by a computer processor causing the processor to perform the operations of: obtaining measurement data for sequence coverage for a biological sample comprising a target sequence; correcting the measurement data for sequence coverage bias, wherein correcting the measurement data comprises performing ploidy-aware baseline correction; based on the corrected measurement data, performing Hidden Markov Model (HMM) segmentation, scoring, and output; based on the HMM scoring and output, performing population-based no-calling and identification of low-confidence regions; and estimating a total copy number value and region-specific copy number value for a plurality of regions.

A further embodiment comprises a system for determining copy number variation of a genomic region at a detection position of a target sequence, comprising: a. a computer processor; and b. a computer-readable storage medium coupled to said processor, the storage medium having instructions tangibly embodied thereon, the instructions when executed by said processor causing said processor to perform the operations of: obtaining measurement data for the sequence coverage for said sample using data generated from mate-pair mappings; correcting the measurement data for sequence coverage bias, wherein correcting the measurement data comprises performing ploidy-aware baseline correction; and based at least on the corrected measurement data, estimating a total copy number value and region-specific copy number value for each of a plurality of genomic regions.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

BRIEF DESCRIPTION OF THE FIGURES

The following drawing(s) are representational of one format for presentation of the data provided from embodiments of the invention. These drawings are not intended to limit in any way the implementation of aspects of the invention as described herein, but rather to aid in clarification of the underlying concepts of the invention.

DETAILED DESCRIPTIONS

Figure 1:
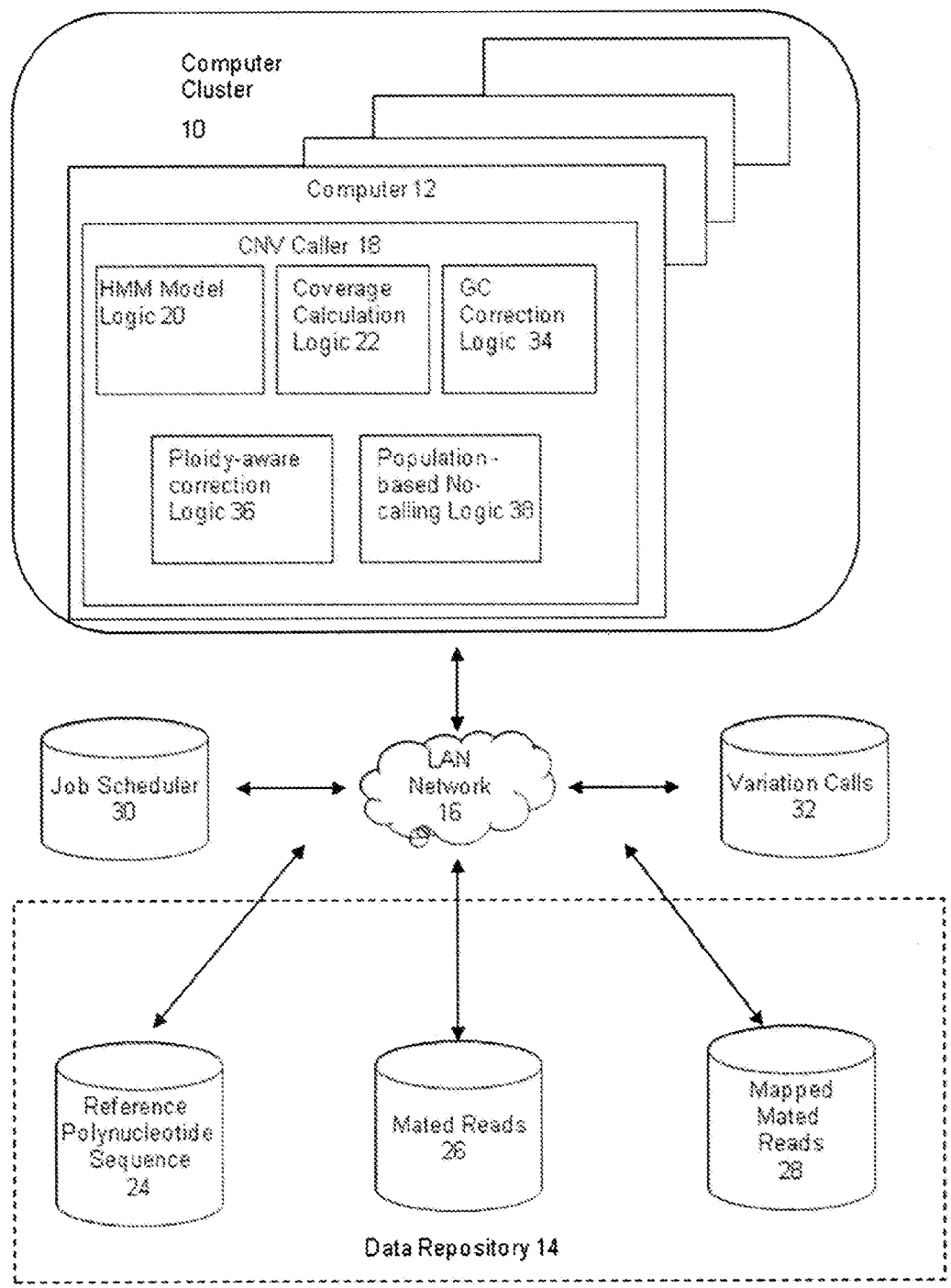
FIG. 1 depicts a generalized block diagram illustrating a system for calling variation in a sample containing target sequences according to an embodiment of the present disclosure.

As used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

Example Sequencing Methods

An example method for sequencing target nucleic acids includes sample preparation involving extracting and fragmenting target nucleic acids from a DNA sample to produce fragmented target nucleic acid templates that will generally include one or more adaptors. The target nucleic acid templates are optionally subjected to amplification methods to form nucleic acid nanoballs, which are typically disposed on a surface or substrate for purpose of analysis. The substrate may yield patterned or random arrangements of nucleic acid nanoballs. Methods for forming nucleic acid nanoballs are described in Published Patent Application Nos. WO2007120208, WO2006073504, WO2007133831, and US2007099208, and U.S. patent application Ser. Nos. 11/679,124; 11/981,761; 11/981,661; 11/981,605; 11/981,793; 11/981,804; 11/451,691; 11/981,607; 11/981,767; 11/982,467; 11/451,692; 12/335,168; 11/541,225; 11/927,356; 11/927,388; 11/938,096; 11/938,106; 10/547,214; 11/981,730; 11/981,685; 11/981,797; 12/252,280; 11/934,695; 11/934,697; 11/934,703; 12/265,593; 12/266,385; 11/938,213; 11/938,221; 12/325,922; 12/329,365; and 12/335,188, all of which are incorporated herein by reference in their entirety for all purposes and in particular for all teachings related to forming nucleic acid nanoballs. Methods for forming arrays of nucleic acid nanoballs are described in Published Patent Application Nos. WO2007120208, WO2006073504, WO2007133831, and US2007099208, and U.S. patent application Ser. Nos. 11/679,124; 11/981,761; 11/981,661; 11/981,605; 11/981,793; 11/981,804; 11/451,691; 11/981,607; 11/981,767; 11/982,467; 11/451,692; 12/335,168; 11/541,225; 11/927,356; 11/927,388; 11/938,096; 11/938,106; 10/547,214; 11/981,730; 11/981,685; 11/981,797; 12/252,280; 11/934,695; 11/934,697; 11/934,703; 12/265,593; 12/266,385; 11/938,213; 11/938,221; 12/325,922; 12/329,365; and 12/335,188, all of which are incorporated herein by reference in their entirety for all purposes and in particular for all teachings related to forming arrays of nucleic acid nanoballs. Methods of using nucleic acid nanoballs in sequencing reactions and in the detection of particular target sequences are also described in U.S. patent application Ser. Nos. 11/679,124; 11/981,761; 11/981,661; 11/981,605; 11/981,793; 11/981,804; 11/451,691; 11/981,607; 11/981,767; 11/982,467; 11/451,692; 12/335,168; 11/541,225; 11/927,356; 11/927,388; 11/938,096; 11/938,106; 10/547,214; 11/981,730; 11/981,685; 11/981,797; 12/252,280; 11/934,695; 11/934,697; 11/934,703; 12/265,593; 12/266,385; 11/938,213; 11/938,221; 12/325,922; 12/329,365; and 12/335,188, each of which is herein incorporated by reference in its entirety for all purposes and in particular for all teachings related conducting sequencing reactions on nucleic acid nanoballs. As will be appreciated, any of the sequencing methods described herein and known in the art can be applied to nucleic acid templates and/or nucleic acid nanoballs in solution or to nucleic acid templates and/or nucleic acid nanoballs disposed on a surface and/or in an array.

Nucleotide sequencing processes are performed on the nucleic acid nanoballs, typically through sequencing-by-ligation techniques, including combinatorial probe anchor ligation ("cPAL") methods, which are described, for example, in Drmanac et al., "Human Genome Sequencing Using Unchained Base Reads on Self-Assembling DNA Nanaoarrays," Science 327:78-81, 2009 (Jan. 1, 2010), as well as in published PCT patent applications WO07/133,831, WO06/138257, WO06/138284, WO07/044,245, WO08/070,352, WO08/058,282, WO08/070,375; and published U.S. patent applications 2007-0037152 and 2008-0221832. In such methods, known labels, such as specific fragments containing a single molecule of a distinguishable fluorophore, are attached as labels according to well-understood rules to the target nucleic acid templates, then resequence indexed on the same types of DNA strand to provide the basis of overlapping data. The sequencing processes referred to herein are merely representative. In another embodiment, tagging is employed. Other processing techniques known or developed in the art may be employed. Then the collection of nucleic acid nanoballs on the substrate is irradiated with radiation to excite the fluorophores sufficient to cause the fluorophores associated with each specific label C, G, A or T to fluoresce at their unique wavelengths, from which a spatial image can be made by a camera, on a (standard or time-delay integration TDI) CCD array or a scanner in lieu of a CCD array, or other electronic current/voltage sensing techniques that may be employed in a sequencing machine. Other sensing mechanisms, such as impedance change sensors, may also be employed. The irradiation may be spectrum specific to excite only a selected fluorophore at a time, which can then be recorded by the camera, or the input to the camera may be filtered to sense and record only spectrum-specific received fluorescent radiation, or all fluorescent radiation can be sensed and recorded simultaneously on a color LCD array and then later analyzed for spectral content at each interrogation site in which there is a nucleic acid construct. The image acquisition yields a series of images of a plurality of interrogation sites that can be analyzed based on spectrum-specific fluorescence intensity through computer processing of the levels of intensity in a process herein denoted as base calling and explained in greater detail herein below. The cPAL and other sequencing methods can also be used to detect specific sequences, such as including Single Nucleotide Polymorphisms ("SNPs") in nucleic acid constructs, (which include nucleic acid nanoballs as well as linear and circular nucleic acid templates). The calls, or identification of the sequences of base calls, e.g., base calls may contain errors for reasons evident by the nature of the sequencing procedure. Using a computer process-based Reed-Solomon error correction, whether in the form of a computer processor performing a Reed-Solomon algorithm or in the form of a comparison mechanism using precomputed expected base call sequences, such as in a look-up table, errors can be identified, "nocall" sequences can be flagged and corrections can be made to yield corrected base call sequences. It should be understood that the magnitude of the sites and structures herein depicted are merely a minute fraction of the magnitude of the sites and structures analyzed on a substrate, as they do not easily admit to illustration. For example the substrate may be a photolithographically etched, surface modified (SOM) 25 mm by 75 mm silicon substrate with grid-patterned arrays of about 300-nm spots for nucleic acid nanoballs binding to increase DNA content per array and improve image information density as compared to random genomic DNA arrays.

Sequencing probes may be detectably labeled with a wide variety of labels. Although the foregoing is primarily directed to embodiments in which the sequencing probes are labeled with fluorophores, it will be appreciated that similar embodiments utilizing sequencing probes comprising other kinds of labels are encompassed by the present invention. Moreover, the processes according to the invention can be employed with unlabeled structures.

In some embodiments, multiple cycles of cPAL (whether single, double, triple, etc.) will identify multiple bases in the regions of the target nucleic acid adjacent to the adaptors. (It is possible to employ a single cycle of cPAL to render multiple bases in an alternate design.) In brief, cPAL methods are repeatedly executed for interrogation of multiple bases within a target nucleic acid by cycling anchor probe hybridization and enzymatic ligation reactions with sequencing probe pools designed to detect nucleotides at varying positions removed from the interface between the adaptor and target nucleic acid. In any given cycle, the sequencing probes used are designed such that the identity of one or more of the bases at one or more positions is correlated with the identity of the label attached to that sequencing probe. Once the ligated sequencing probe, and hence the base or bases at the interrogation position or positions are detected, the ligated complex is stripped off of the nucleic acid nanoballs and a new cycle of adaptor and sequencing probe hybridization and ligation is conducted. By this mechanism, oversampled data are obtainable.

Selected Definitions

"Adaptor" refers to an engineered construct comprising "adaptor elements" where one or more adaptors may be interspersed within target nucleic acid in a library construct. The adaptor elements or features included in any adaptor vary widely depending on the use of the adaptors, but typically include sites for restriction endonuclease recognition and/or cutting, sites for primer binding (for amplifying the library constructs) or anchor primer binding (for sequencing the target nucleic acids in the library constructs), nickase sites, and the like. In some aspects, adaptors are engineered so as to comprise one or more of the following: 1) a length of about 20 to about 250 nucleotides, or about 40 to about 100 oligonucleotides, or less than about 60 nucleotides, or less than about 50 nucleotides; 2) features so as to be ligated to the target nucleic acid as at least one and typically two "arms"; 3) different and distinct anchor binding sites at the 5' and/or the 3' ends of the adaptor for use in sequencing of adjacent target nucleic acid; and 4) optionally one or more restriction sites. In one aspect, adaptors can be interspersed adaptors. By "interspersed adaptors" is meant herein oligonucleotides that are inserted at spaced locations within the interior region of a target nucleic acid. In one aspect, "interior" in reference to a target nucleic acid means a site internal to a target nucleic acid prior to processing, such as circularization and cleavage, that may introduce sequence inversions, or like transformations, which disrupt the ordering of nucleotides within a target nucleic acid. Use of interspersed adaptors facilitates sequence reconstruction and alignment, as sequence runs of 10 bases each from a single adaptor can allow 20, 30, 40, etc. bases to be read without alignment, per se.

"Amplicon" means the product of a polynucleotide amplification reaction. That is, it is a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle dependant amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and US Pub. No. 2006/0024711).

The term "base" when used in the context of identification refers to the purine or pyrimidine group (or an analog or variant thereof) that is associated with a nucleotide at a given position within a target nucleic acid. Thus, to call a base or to identify a nucleotide both refer to determining a data value identifying the purine or pyrimidine group (or an analog or variant thereof) at a specific position within a target nucleic acid. The purine and pyrimidine groups include the four main nucleotide bases of C, G, A, and T.

"Polynucleotide", "nucleic acid", "oligonucleotide", "oligo" or grammatical equivalents used herein refers generally to at least two nucleotides covalently linked together in a linear fashion. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones.

The term "reference polynucleotide sequence", or simply "reference", refers to a known sequence of nucleotides of a reference organism. The reference may be an entire genome sequence (e.g., a reference genome) of a reference organism, a portion of a reference genome, a consensus sequence of many reference organisms, a compilation sequence based on different components of different organisms, a collection of genome sequences drawn from a population of organisms, or any other appropriate sequence. The reference may also include information regarding variations of the reference known to be found in a population of organisms. The reference organism may also be specific to the sample being sequenced, possibly a related individual or the same individual, separately drawn (possibly normal to complement cancer sequence).

"Sample polynucleotide sequence" refers to a nucleic acid sequence of a sample or target organism derived from a gene, a regulatory element, genomic DNA, cDNA, RNAs including mRNAs, rRNAs, siRNAs, miRNAs, and the like, and/or from fragments thereof. A sample polynucleotide sequence may be a nucleic acid from a sample, or a secondary nucleic acid such as a product of an amplification reaction. For a sample polynucleotide sequence or a polynucleotide fragment to be "derived" from a sample polynucleotide (or any polynucleotide) can mean that the sample sequence/polynucleotide fragment is formed by physically, chemically, and/or enzymatically fragmenting a sample polynucleotide (or any other polynucleotide). To be "derived" from a polynucleotide may also mean that the fragment is the result of a replication or amplification of a particular subset of the nucleotide sequence of the source polynucleotide.

A "read" refers to a set of one or more data values that represent one or more nucleotide bases. A "mated read" (also referred to as "mate-pair") refers generally to a set of individual nucleotide reads originating from two distinct regions of genomic sequence (arms) located at opposite ends of a DNA fragment across a distance of a few hundred or thousand bases. The mated read may be generated during sequencing from a fragment of a larger contiguous polynucleotide (e.g., DNA) obtained from the sample organism to be variation called and/or reassembled.

"Mapping" refers to one or more data values that relate a read (e.g., such as a mated read) to zero, one or more locations in the reference to which the read is similar, e.g., by matching the instantiated read to one or more keys within an index corresponding to a location within a reference.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of less than about 1M, more usually less than about 500 mM and may be less than about 200 mM. Hybridization temperatures can be as low as 5° C., but are typically greater than 22° C., and more typically greater than about 30° C., and typically in excess of 37° C.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921.

"Logic" refers to a set of instructions which, when executed by one or more processors (e.g., CPUs) of one or more computer systems, are operable to perform one or more functionalities and/or return data in the form of one or more results and/or data that is sued by other logic elements. In various embodiments and implementations, any given logic may be implemented as one or more software components that are executable by one or more processors (e.g., CPUs), as one or more hardware components such as Application-Specific Integrated Circuits (ASICs) and/or Field-Programmable Gate Arrays (FPGAs), or as any combination of one or more software components and one or more hardware components. The software component(s) of any particular logic may be implemented, without limitation, as a standalone or client-server software application, as one or more software modules, as one or more libraries of functions, and as one or more static and/or dynamically-linked libraries. During execution, the instructions of any particular logic may be embodied as one or more computer processes, threads, fibers, and any other suitable run-time entities that can be instantiated in the hardware of one or more computing devices and can be allocated computing resources such as memory, CPU time, storage space, and network bandwidth.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Probe" means generally an oligonucleotide that is complementary to an oligonucleotide or target nucleic acid under investigation. Probes used in certain aspects of the claimed invention are labeled in a way that permits detection, e.g., with a fluorescent or other optically-discernable tag.

"Sequence determination" (also referred to as "sequencing") in reference to a target nucleic acid means determination of information relating to the sequence of nucleotide bases in the target nucleic acid. Such information may include the identification or determination of partial as well as full sequence information of the target nucleic acid. The sequence information may be determined with varying degrees of statistical reliability or confidence. In one aspect, sequencing includes the determination of the identity and ordering of a plurality of contiguous nucleotides in a target nucleic acid starting from different nucleotides in the target nucleic acid. Sequencing and the various steps thereof may be performed by a sequencing machine that comprises a reaction subsystem and an imaging subsystem. The reaction subsystem includes flow devices (on which biochemical reactions take place between various reagents, buffers, etc. and a biochemical sample or fragments derived therefrom) and various other components (e.g., such tubing, valves, injectors, actuators, motors, and the like) that are configured to dispose the reagents, buffers, sample fragments, etc. on, or in, the flow device. The imaging subsystem comprises a camera, a microscope (and/or appropriate lenses and tubing), a stage that holds the flow device during sequencing, and various other components (e.g., such as motors, actuators, robotic arms, etc.) for placing and adjusting the flow device on the stage as well as adjusting the relative positions of the camera and the microscope.

"Target nucleic acid" means a nucleic acid of (typically) unknown sequence from a gene, a regulatory element, genomic DNA, cDNA, RNAs including mRNAs, rRNAs, siRNAs, miRNAs and the like and fragments thereof. A target nucleic acid may be a nucleic acid from a sample, or a secondary nucleic acid such as a product of an amplification reaction. Target nucleic acids can be obtained from virtually any source and can be prepared using methods known in the art. For example, target nucleic acids can be directly isolated without amplification, isolated by amplification using methods known in the art, including without limitation polymerase chain reaction (PCR), strand displacement amplification (SDA), multiple displacement amplification (MDA), rolling circle amplification (RCA), rolling circle amplification (RCR) and other amplification (including whole genome amplification) methodologies. Target nucleic acids may also be obtained through cloning, including but not limited to cloning into vehicles such as plasmids, yeast, and bacterial artificial chromosomes. In some aspects, the target nucleic acids comprise mRNAs or cDNAs. In certain embodiments, the target DNA is created using isolated transcripts from a biological sample. Target nucleic acids can be obtained from a sample using methods known in the art. As will be appreciated, the sample may comprise any number of substances, including, but not limited to, bodily fluids such as, for example, blood, urine, serum, lymph, saliva, anal and vaginal secretions, perspiration and semen, of virtually any organism, with mammalian samples being preferred and human samples being particularly preferred. Methods of obtaining target nucleic acids from various organisms are well known in the art. Samples comprising genomic DNA of humans find use in many embodiments. In some aspects such as whole genome sequencing, about 20 to about 1,000,0000 or more genome-equivalents of DNA are preferably obtained to ensure that the population of target DNA fragments sufficiently covers the entire genome.

Example Methods of Genome Sequencing and CNV Estimation

The present invention is directed to methods for estimating copy number variants of genomic regions of interest at a detection position in a target sequence in a sample, which find use in a wide variety of applications as described herein.

The methods of the present disclosure may also include extracting and fragmenting target nucleic acids from a sample and/or sequencing the target nucleic acids for which CNV estimation is performed. These fragmented nucleic acids are used to produce target nucleic acid templates that generally include one or more adaptors. The target nucleic acid templates are subjected to amplification methods to form nucleic acid concatemers such as, for example, nucleic acid nanoballs.

In one aspect, nucleic acid templates can comprise target nucleic acids and multiple interspersed adaptors, also referred to herein as "library constructs," "circular templates", "circular constructs", "target nucleic acid templates", and other grammatical equivalents. The nucleic acid template constructs are assembled by inserting adaptors molecules at a multiplicity of sites throughout each target nucleic acid. The interspersed adaptors permit acquisition of sequence information from multiple sites in the target nucleic acid consecutively or simultaneously.

In further embodiments, nucleic acid templates formed from a plurality of genomic fragments can be used to create a library of nucleic acid templates. Such libraries of nucleic acid templates will in some embodiments encompass target nucleic acids that together encompass all or part of an entire genome. That is, by using a sufficient number of starting genomes (e.g. genomes of cells), combined with random fragmentation, the resulting target nucleic acids of a particular size that are used to create the circular templates sufficiently "cover" the genome, although as will be appreciated, on occasion, bias may be introduced inadvertently to prevent the entire genome from being represented.

Further embodiments and examples of methods of constructing nucleic acid templates are described in U.S. application Ser. Nos. 11/679,124; 11/981,761; 11/981,661; 11/981,605; 11/981,793; 11/981,804; 11/451,691; 11/981,607; 11/981,767; 11/982,467; 11/451,692; 12/335,168; 11/541,225; 11/927,356; 11/927,388; 11/938,096; 11/938,106; 10/547,214; 11/981,730; 11/981,685; 11/981,797; 12/252,280; 11/934,695; 11/934,697; 11/934,703; 12/265,593; 12/266,385; 11/938,213; 11/938,221; 12/325,922; 12/329,365; and 12/335,188, each of which is herein incorporated by reference in its entirety for all purposes and in particular for all teachings related to constructing nucleic acid templates of the techniques described herein.

Nucleic acid templates of the techniques described herein may be double stranded or single stranded, and they may be linear or circular. In some embodiments, libraries of nucleic acid templates are generated, and in further embodiments, the target sequences contained among the different templates in such libraries together cover all or part of an entire genome. As will be appreciated, these libraries of nucleic acid templates may comprise diploid genomes or they may be processed using methods known in the art to isolate sequences from one set of parental chromosomes over the other. As will also be appreciated by those of skill in the art, single stranded circular templates in libraries may together comprise both strands of a chromosome or chromosomal region (i.e., both "Watson" and "Crick" strands), or circles comprising sequences from one strand or the other may be isolated into their own libraries using methods known in the art.

For any of sequencing methods known in the art and described herein using nucleic acid templates, the techniques described herein provide methods for determining at least about 10 to about 200 bases in target nucleic acids. In further embodiments, the techniques described herein provide methods for determining at least about 20 to about 180, about 30 to about 160, about 40 to about 140, about 50 to about 120, about 60 to about 100, and about 70 to about 80 bases in target nucleic acids. In still further embodiments, sequencing methods are used to identify 5, 10, 15, 20, 25, 30 or more bases adjacent to one or both ends of each adaptor in a nucleic acid template.

Overview of Techniques for CNV Calling

CNV calling for normal and tumor samples share some features but also have differences. In some embodiments, both types of samples are subject to the following three steps.
1) Computation of sequence coverage.
2) Estimation and correction of bias in coverage:
 a. Modeling of coverage bias;
 b. Correction of modeled bias;
 c. Coverage smoothing.
3) Normalization of coverage by comparison to a baseline sample or set of samples.

Following this, both normal and tumor samples are segmented using Hidden Markov Models (HMMs), but with different models for the two sample types in the following steps:
4A) HMM segmentation, scoring and output for normal samples;
4B) Modifications to HMM segmentation, scoring and output for tumor samples;

Finally, normal samples are subjected to a 'no-calling' process which identifies CNV calls that are suspect in the following step:
5) Population-based no-calling/identification of low-confidence regions.

In various embodiments, the above steps of CNV calling may be performed by different types of logic that is executed on one or more computer systems. Examples of such logic elements are described hereinafter with respect to FIG. 1.

Example Embodiments of Techniques for Cnv Calling

1. Computation of Sequence Coverage

As used hereinafter, "DNB" refers to the sequence of a nucleic acid nanoball from which one or more reads (e.g., such as a mated read) have been sequenced. It is noted that in the reads sequenced from a biological sample or fragments thereof, a DNB is represented as one or more reads that may or may not cover the entire sequence that constitutes the DNB. For example, in one embodiment the DNB is represented by a mated read that comprises two or more arm reads, from opposite ends of the DNB, that are separated by an unknown sequence of a few hundred bases.

In one aspect, all mate-pair constraint-satisfying paired-end (e.g., full DNB) mappings are used to compute sequence coverage. In a certain embodiment, a unique paired end mapping contributes a single count to each base of the reference that is aligned to the DNB. A reference base aligned to a nonunique paired-end mapping is weighted (e.g., is given a fractional count) based on the estimated probability that the mapping is the correct location of the DNB in the reference. Fractional attribution of DNBs in proportion to the confidence in each mapping thus provides the ability to give reasonable coverage estimates in regions where mappings are non-unique.

In one aspect, each position i of the reference genome R receives the following coverage value $c_1$:

$$c_i = \Sigma_{m \in M_i} P(DNB|R,m)/(\alpha + \Sigma_{n \in N(m)} P(DNB_m|R,n))$$

where $M_i$ is the set of mappings over all DNBs such that a called base in each mapping is aligned to position i, $DNB_m$ is the DNB described by mapping m, N(m) is the set of all mappings involving $DNB_m$, and α is the probability that a DNB is generated in a fashion that does not allow it to map to the reference.

According to the techniques described herein, computer logic (e.g., such as CNV caller 18 in FIG. 1 and/or a component thereof such as coverage calculation logic 22) computes the coverage values for the positions (or loci) in the reference genome based on the DNB mappings. The computer logic then includes the computed coverage values in measurement data that is used in subsequent processing.

2. Estimation and Correction of Bias in Coverage (Sample-Internal Manipulation of Coverage)

Currently, genome sequencing can result in coverage bias that may affect estimation of copy number. One element of the bias involves the GC content over intervals approximately the length of the initial DNA fragment that becomes a DNB (e.g., approximately 400 bp), though other factors are known as well. In one embodiment, it is generally preferred to model and correct for such biases prior to or as part of copy number estimation.

In another embodiment, it is desirable to apply some smoothing to short scale fluctuations in coverage, which may be at least partly specific to an individual library of circles or DNBs.

There are several approaches to bias correction and smoothing that may be used. All of the operations and steps in these approaches may be performed by computer logic (e.g., such as CNV caller 18 in FIG. 1 and/or a component thereof such as GC correction logic 34) based on measurement data that includes, but may not be limited to, coverage values for each position in the reference genome.

Approach 1: Post-Hoc Coverage Correction:

In one embodiment, the sequence coverage as described above is smoothed by window-averaging and then adjusted to account for GC bias in the library construction and sequencing process.

Window-averaging is performed by computing the mean of the unsmoothed coverage values for every position within a window. For window length N, the averaged coverage reported at position i is:

$$\bar{c}_i = \Sigma_{j=i-N/2}^{i+(N/2-1)} c_j/N$$

From such smoothed coverage, in one embodiment a set of adjustment factors is computed. GC content is computed over 1000 base pair windows (i.e. N=1000) every 1000 bases along each reference contig. Each window is assigned to one of 1000 bins based on the number of Gs and Cs present in the portion of the reference covered by the window. Let W be the set of tabulated windows (equivalently, their center positions)
and $W_b$ be the set of windows with [G+C]=b. The average uncorrected coverage for each bin b, is $\hat{c}_b$, determined as:

$$\hat{c}_b = \Sigma_{w\ in\ W_b} \bar{c}_w/|W_b|$$

Letting $\hat{C}$ be the mean coverage over the full genome ($\hat{C} = \Sigma_{w \in W} \bar{c}_w/|W|$), for each GC bin b a correction factor $f_b$ is given as:

$$f_b = \hat{C}/\hat{c}_b$$

In another embodiment, the correction factors may be estimated using further smoothing operations. This may provide, e.g., greater robustness to small-sample variation or overfitting. For instance, the terms $f_b$ may be subjected to smoothing using splines, piecewise regression, sliding window averaging, LOESS, etc.

$$\hat{f}, \hat{f}_\gamma = LOESS(f(\gamma)) c_i' = c_i/\hat{f}_{gc_i}$$

The corrected, smoothed coverage for a 1000-base window centered at position i, assigned to bin $b_i$, is then computed as follows:

$$\bar{c}_i' = \bar{c}_i * f_{b_i}$$

Corrected, smoothed coverage for larger windows, of length l=n*1000 (n being a positive integer) can be computed as the mean over the values for the contained 1000-base windows.

In addition to the above, it should be clear that many embodiment variations can exist. Window sizes and shifts may be changed. Certain positions may be ignored (and the corresponding windows either enlarged to achieve a fixed number of accepted positions or means taken only on the accepted positions), based on various characteristics such as structural annotation (e.g. repeats), excess or insufficient variability among multiple samples, accessibility/uniqueness under the criteria used for mapping, depth of coverage in simulated data (measuring mapability) etc. The mathematical mean may be replaced by median, mode or other summary statistics in appropriate locations. Correction factors may be computed based on the coverage of a single position rather than the average coverage for a window, with smoothing/averaging being applied after correction rather than before.

This class of exemplary approaches may be extended to consider multiple predictors of coverage by computing correction factors for multidimensional binning of positions on the genome. For example, not only GC content on the scale of a full DNB can be considered, but also on the scale of the individual DNB arms. Alternatively, separate correction factors can be computed for each predictor, corresponding to an assumption of independence of the effects.

Approach 2: Mapping-Level Coverage Correction:

In the second approach to bias correction and smoothing, individual mappings are given an additional weighting factor to compensate for bias prior to smoothing. DNBs (mappings) that are more likely due to the bias than expected of a uniform random sampling are downweighted, while DNBs that are less likely due to the bias are upweighted (and may contribute more than a full count to the coverage computation). Letting $q_m$ be the correction factor for mapping m (defined below), corrected coverage at position i can be computed as:

$$c_i' = \sum_{m \in M} q_m * P(DNB|R,m) \bigg/ \bigg( \alpha + \sum_{n \in N(m)} P(DNB_m|R,n) \bigg)$$

The correction factor $q_m$, is determined based on the odds ratio derived from a logistic regression model fit to discriminate mappings in the real dataset from mappings in a dataset simulated with uniform random sampling of the reference genome. The model predicts whether a given mapping is real or simulated based on a b-spline of order 1 (piecewise linear) with knots at every fifth percentile of the distribution of GC content in the combined (real+simulation) dataset. For example, the corresponding R code is:
model <-glm(isReal~
bs(dnbGCpcnt,df=20,degree=1,Boundary.knots=c(0,1)),
    data=d,family=binomial)
where the input dataset, d, is composed of equal numbers of records of unique paired-end simulated mappings and records of unique paired-end real mappings. For simulation records, isReal=0; for real records, isReal=1. dnbGCpcnt is the percent GC in the portion of the reference spanned by the mapping.

Given the resulting model, the correction factor $q_m$ is taken as the model-predicted sim:real odds ratio given the GC percentage for mapping m. Thus, if a given GC percentage is three times more likely in real data than in simulated data, real mappings with that GC content are weighted by a factor of ⅓.

A similar odds-ratio based factor could be determined using a logistic model accounting for many properties of a mapping, including factors such as:
  Composition of entire fragment (~500 bp);
  Composition of genomic segments in final DNB (~80 bp);
  Choice of base at every position in final DNB;
  Oligomers at specific locations in original fragment;
  Sequences adjacent to adaptors (ligation efficiency impact, e.g.);
  Sequences at typical locations of restriction enzyme cut sites;
  Predicted physical characteristics;
  Melting temperatures;
  Flexibility/curvature;
  Measured/measurable/predicted characteristics of regions of the genome such as Histone binding and Methylation.

The model could include not only linear effects of single measurements but also various transformations of single measurements (e.g. piecewise linear or polynomial fitting or binning) and interaction terms.

In a certain embodiment, model-corrected coverage is then smoothed via sliding window averaging, and rounded to an integer. The width of the window is configurable; the default value is 2 kb. Average coverage is by default reported for abutting windows (e.g. for window shifts equal to the window width), but other shift amounts can be employed. Average corrected coverage is reported for the position at the midpoint of each window.

Each contig (or a region of contiguous loci) of the reference genome is processed separately, so that with default width=2k each contig>2 kb in length results in coverage values at 1 kb, 3 kb, 5 kb, . . . relative to the start of the contig. Thus, for such a position i, smoothed coverage is given as:

$$\overline{c}'_i = \sum_{j=i-1000}^{i+999} c'_j / 2000$$

The first window of each contig starts at the first base of the contig; the window is shifted until the end of the window would be beyond the end of the contig. Since the starting position of a contig relative to its chromosome may be an arbitrary value, the chromosome position reported for a given window may not be a nice round number.

Approach 3: GC Normalization Process

In one embodiment, a computer logic (e.g., such as CNV caller 18 in FIG. 1 or a component thereof such as GC correction logic 34) estimates and corrects bias in coverage as follows.

First, GC content is computed for the 1000-base window centered at every point of the genome (excluding positions less than 500 bases from the ends of contigs). For example, a function isGC(j) can be set to 1 if the base at position j is G or C and 0 otherwise, and the GC content at position i, $gc_i$, can be computed as follows:

$$gc_i = \sum_{j=i-500}^{i+499} isGC(j)$$

Positions less than 500 bases from either end of a contig are not considered during the estimation of the GC correction factors.

Next, for each possible GC value γ, the mean coverage $\tilde{C}_\gamma$ is determined for positions with $gc_i=\gamma$. Letting $n_\gamma$ be the number of positions i in the genome with $gc_i=\gamma$, the mean coverage may be computed as follows:

$$\tilde{C}_\gamma = \frac{\sum_{gc_i=\gamma} c_i}{n_\gamma}$$

In example implementations, the positions with coverage>500 may be excluded.

Next, the above two steps are completed for a simulation. Using the "*" superscript to indicate simulation results, the simulated mean coverage may be determined as follows:

$$\tilde{C}_\gamma^* = \frac{\sum_{gc_i=\gamma} c_i^*}{n_\gamma}$$

It is noted that the above result is not entirely flat due to the GC content of ubiquitous repeats, microsatellite regions, etc., not being the similar to the genome as a whole.

Next, the ratio of sample coverage to simulation coverage is computed for each GC value, adjusting for the overall average coverage of the sample and the simulation ($\overline{c}$ and $\overline{c}^*$ respectively). For example, this ratio may be computed as follows:

$$f_\gamma = \frac{\tilde{C}_\gamma}{\tilde{C}_\gamma^*} * \frac{\overline{c}^*}{\overline{c}}$$

Next, a smoothed coverage ratio is obtained as a function of GC, $\hat{f}_\gamma$. For example, a locally weighted polynomial regression may be used as follows:

$$\hat{f}_\gamma = LOESS(f(\gamma))$$

As a local regression operation, LOESS smoothing is performed except in numerically unstable regions where LOWESS is performed instead.

Next, the GC-correct (single-base) coverage at every position of the genome is computed as follows:

$$c_i' = c_i \hat{f}_{gc_i}$$

Near the ends of the contigs, 'missing bases' are filled in with genome-wide average GC content. If the GC content of the window for a given position is too extreme (i.e. <20% or >80% GC), the coverage value is treated as unknown (e.g., as missing data).

Window-smoothing is performed by taking the mean of $\hat{c}_i$ for each position i within a given window. Windows are tiled (adjacent, non-overlapping), with the choice of window boundaries as defined in the section below titled "Window Boundary Definition". That is, for a window corresponding to the interval [i,j), the average corrected coverage $\bar{c}_{i,j}'$ is computed as $$\bar{c}_{i,j}' = \sum_{k=i}^{j-1} c_k' / (j - i)$$

It is noted that for notational simplicity, in the sections below the "j" subscript is dropped, i.e. $\bar{c}_i'$ is used in place of $\bar{c}_{i,j}'$, as there is at most one window starting at position i.

3. Normalization of Coverage by Comparison to a Baseline Sample

In various embodiments, the operations, computations, and method steps described in this section (Section 3) can be performed by computer logic such as, for example, CNV variant caller 18 in FIG. 1 and/or by a component thereof such as, for example, ploidy-aware correction logic 36.

In some embodiments, bias in coverage not corrected by the adjustments described above may be taken into account by comparison to a baseline sample. However, in order to obtain coverage proportional to absolute copy number, the baseline sample may be adjusted according to the copy number in said sample.

Letting $d_i'$ and $p_i$ be the coverage and ploidy at position i for the baseline sample, and $\tilde{d}$ be an estimate of the typical diploid coverage for the baseline sample, the bias correction factor $b_i$ can be determined as follows:

$$b_i = \frac{\tilde{d}}{d_i'} * \frac{p_i}{2}$$

(In one implementation, $\tilde{d}$ may be taken as the 45% percentile of windows in the autosome.) The normalized corrected coverage $\bar{c}_i''$ is then computed as follows:

$$\bar{c}_i'' = \bar{c}_i' * b_i$$

If $p_i=0$ (in which case $d_i$ is due to mismappings and not a reliable indicator of coverage behavior in this location), $\bar{c}_i''$ as treated as missing. This correction of bias performed based on known or hypothesized ploidy and coverage at position(s) in a baseline sample is referred to herein as "ploidy-aware baseline correction." Specifically, the ploidy-aware baseline correction adjusts the coverage value for each position (or locus) in a baseline or reference sample based on the ploidy and coverage detected for that same position in the target polynucleotide sequence of the target sample, as an element of using the baseline values to correct the coverage in the sample to be analyzed.

In some implementations, the sequences of a group of samples may be used, rather than a single sample, as the baseline, in order to reduce sensitivity to fluctuations due to sampling (statistical noise) or due to library-specific biases. For example, the following for the set of baseline samples S may be used:

$$p_i = \sum_{s \in S} p_i^s$$

$$d_i = \sum_{s \in S} d_i^s$$

where $p_i$, the ploidy at window i. Ideally, this would be the true ploidy for the baseline sample for this window. However, since it is not known, it needs to be estimated.

Thus, in one implementation, a baseline generation process includes CNV-calling for each baseline genome, using a simulation where copy number is 2 for autosomes and gender-appropriate for sex chromosomes. Using a simulation as the baseline provides an indirect means of correcting for variation in mapability of the genome, e.g. regions corresponding to high-copy, high-identity repeats that "overflow" during mapping. However, this may not address coverage bias due to biochemistry. In regions of moderate coverage bias, and where the length scale of bias is short relative to the length of the window, the baseline genome(s) will be called at the correct ploidy and consequently the correction factor will appropriately compensate for the bias. However, regions with a sustained bias resulting in coverage being >50% of the diploid-average away from the true ploidy will have their copy number miscalled on the baseline genomes; this results in a baseline "correction" that reinforces the tendency to call CNVs at this location, i.e. results in robust/consistent miscalling of abnormal ploidy. In other implementations, estimation of the ploidy of baseline genomes may be based on external information (e.g. chip-based CNV calls), manual curation, or an automated process that attempts to determine population patterns by simultaneous analysis of multiple genomes.

In other embodiments, $\tilde{d}$ may be determined in various ways. For instance, it may be taken as the median of positions estimated to have ploidy 2 in a previous estimation of ploidy for the baseline sample, as the modal coverage value, or as some fixed percentile of the coverage over the whole genome (perhaps adjusted for male vs female samples). A group of samples may be used, rather than a single sample, as the baseline. In this case, $d_i'$ and $p_i$ be might be taken as the sums of coverage and ploidy over all baseline samples at reference position i, and $\tilde{d}$ may be determined as the sum over samples of typical diploid coverage. Alternatively, a mean or median of values computed for each of several baseline samples may be used in order to provide estimates that were less sensitive to differences in coverage among baseline samples.

If no samples are input as baseline, then $\bar{c}_i''$ is simply set as follows:

$$\bar{c}_i'' = \bar{c}_i'$$

4A. HMM Segmentation, Scoring and Output for Normal Samples

In various embodiments, the operations, computations, and method steps described in this section (Section 4A) can be performed by computer logic such as, for example, CNV variant caller 18 in FIG. 1 and/or a component thereof such as HMM model logic 20.

In certain aspects, there are many approaches to segmenting a quantitative time-series that can be applied to calling CNVs—that is, that can be applied to coverage data produced by the above sequence of steps. Hidden Markov Models (HMMs) provide one such approach with certain appealing properties (obvious model fitting methods, flexible models, natural confidence measures, ability to constrain models, ability to incorporate a variety of models of coverage generation), wherein states correspond to copy number levels, emissions are some form of coverage (observed/corrected/relative), and transitions between states are changes in copy number. Emission probabilities may be modeled as Poisson distributions, negative binomial, mixtures of Poisson distributions, piecewise models fit to the data, etc. Choice of model can be made with goodness of fit measures and cross-validation. In one embodiment, it may be desirable to smooth per-position coverage values over longer (sliding) windows, though it is desirable for the window width to be considerably narrower than the desired minimal event size. In one embodiment, it may be desirable to constrain the models in various ways, e.g. require that the expected outputs of each copy number level (e.g. means of emission probabilities of states in an HMM) be consistent multiples of one another, as expected from discrete copy number changes. In one embodiment, it may be desirable to include in the expected coverage distributions components corresponding to 'contamination' of a tumor sample with normal tissue, or to capture tumor heterogeneity, e.g. with mixture models.

In another aspect, it is possible to integrate other signals (e.g., parameters and values thereof) into CNV detection, or to use other signals (e.g., data values) to confirm or filter output from a coverage-based CNV detector. Such other signals include the presence of anomalous mate pairs at the boundary between two copy number levels, or changes in allele balance in heterozygous positions.

In yet another aspect, a particular HMM-based method for estimating the copy number may be used based on a function of reference genome position. For example, GC-corrected, window-averaged, normalized coverage data, $\bar{c}_i''$, may be input to an HMM whose states correspond to integer ploidy (copy number). Copy number along the genome may be estimated as the ploidy of the sequence of most likely states according to the model. Various scores are computed based on the posterior probabilities generated by the HMM. This aspect is described in more detail below.

Model Definition:

A fully-connected HMM with states corresponding to ploidy 0, ploidy 1, ploidy 2, . . . , ploidy 9, and ploidy "10 or more" is defined by a matrix of transition probabilities, initial state probabilities, and the emission probabilities. (In various embodiments, the exact number of states can be modified.)

Coverage distributions (i.e. state emission probabilities) are modeled as a negative binomial, which can be parameterized by the mean and variance of the distribution for each state.

Model Estimation:

In principle, model parameters can all be estimated by estimation-maximization (EM) by the Baum-Welch algorithm; however, in practice, unconstrained estimation (especially of coverage distributions) does not always provide satisfactory results. To address this issue, in one embodiment initial values are chosen and subsequent updates are constrained to reflect the following assumptions: coverage is assumed to depend on the number of copies of a given reference segment in the genome of interest; copy number is assumed to be integer valued; coverage is assumed to be linearly related to copy number; the majority of the genome is assumed to be diploid, so that the "typical" value for the autosome can be used to fix the mean coverage for ploidy=2; for states corresponding to ploidy>=1, the standard deviation of a state is assumed to be proportional to the mean of the state; for the state corresponding to ploidy=0, a separate variance can be used to allow for the impact of mis-mappings and non-unique mappings. Given these constraints and assumptions, there are only two free parameters regarding the coverage distributions, namely a single value relating coverage to standard deviation for ploidy>=1, and another variance parameter for ploidy=0.

In one implementation, transition probabilities can be estimated from the data but the default behavior would be to maintain the initial values. The initial values may be set by the user; if not set, initial values may default to $t_{ij}$=0.01, e.g. a one percent chance of being in state j at time t+1 given that the model is in state i at time t for any distinct states i and j. In another implementation, transition probabilities could be estimated from the data but the risk of over-fitting is high. Consequently, a set of default values may be used, such that the probability of transition from one state to another at any "time" (window) is set to 0.003, and the probability of remaining in a given state is taken as 1−0.003*10=0.97.

Initial state probabilities are all set to 1 divided by the number of states.

The mean of the emission (coverage) distribution for a state with ploidy n is initialized as follows, except as noted below:

$$\mu_n = n*\bar{\bar{c}}''/2$$

where $\bar{\bar{c}}''$ is the median of $\bar{c}_i''$ for all positions at which normalized smoothed corrected coverage has been computed. To allow for the presence of some apparent coverage due to mismappings, in one embodiment $\mu_0$ is set to 1, i.e., $\mu_0$=1; in another embodiment $\mu_0$ may be set as $\mu_0$=0.1*$\bar{\bar{c}}''$. Initial estimates of the means are not updated during subsequent model fitting.

The initial variance of the ploidy 2 state is set to:

$$\sigma_2^2 = 3*\mu_2 = 3*\bar{\bar{c}}''$$

$$\bar{\bar{c}}''\bar{c}_i''\mu_0 = 1.$$

In some implementations, variance for other states is set so that standard deviations will be proportional to the means:

$$\sigma_n^2 = \sigma_2^2 *(n/2)^2$$

In other implementations, the initial variance of the negative binomial may be set as follows $$\sigma_n^2 = 3*\mu_n.$$

The variance-determining parameters are updated by EM until the model has 'converged', e.g. the change in log likelihood of the data given the model between successive iterations is sufficiently small, e.g., below a certain threshold.

In another aspect, the initial variance estimates can be updated during model fitting (using EM with the modifications to constrain the mean), but are constrained to never be smaller than the above. This model operates under the assumption that the majority of the genome is diploid, that the median of the entire distribution will be near the median, and thus the mean, of the diploid portion of the genome, and that copy numbers are strictly integer values. In this aspect, adjustments may need to be made over time to estimate copy number for highly aneuploid samples, for tumors with substantial 'normal contamination', and for regions that are not unique in the reference.

The updating procedure is allowed to iterate until it has 'converged', e.g. the change in log likelihood of the data given the model changes less than 0.001 between successive iterations.

Ploidy Inference, Segmentation and Scoring:

In a further embodiment, after convergence of the estimation procedure, the usual HMM inference computations are performed. The final result is based on the most likely state at each position. (A standard alternative is to assign ploidy corresponding to the states of the most likely single path.)

In one embodiment, the "calledPloidy" of each position in the input is taken to be that of the most likely state at that position. The "ploidyScore" is given as a phred-like score (e.g., a logarithm-based score measured in decibels dB) reflecting the confidence that the called ploidy is correct. The "CNVTypeScore" is given as a phred-like score reflecting the confidence that the called ploidy correctly indicates whether the position has decreased ploidy, expected ploidy, or increased ploidy relative to the nominal expectation (diploid except that sex chromosomes in males are expected haploid). Additional scores at each position ("scorePloidy=0", "scorePloidy=1" etc) reflect the probability of each possible ploidy; the score at each state is int(10 log 10 ($L_{is}$)) where $L_{is}$ is the likelihood of being in state s at position i.

In another embodiment, 'segment' is a sequence of adjacent positions that have the same called ploidy. The 'begin' and 'end' positions of the segment are taken as outside the midpoints of the beginning and ending windows. Each segment is given a ploidyScore equal to the average of the ploidyScores for the positions in the segment, and a CNVTypeScore that is the mean of the CNVTypeScores for the positions in the segment.

Precise definitions and justification of the above scores are given the section below titled "Score Computation".

4B. Modifications to Hmm Segmentation, Scoring and Output for Tumor Samples (Tumor CNV Approach)

In various embodiments, the operations, computations, and method steps described in this section (Section 4B) can be performed by computer logic such as, for example, CNV variant caller 18 in FIG. 1 and/or a component thereof such as HMM model logic 20.

In certain aspects, copy-number calling in tumor samples poses several challenges to the methods described so far. Due to the possibility of high average copy number, it is not advisable to assume that diploid ('normal') regions of the genome will have coverage near the sample median. Even if the typical coverage for a diploid region could be determined (e.g. by analysis of minor allele frequency), the expected change in coverage for an increase or decrease of a single copy is not necessarily 50% of this value, due to the possibility of an unknown amount of contamination from adjacent or mixed-in normal cells ('normal contamination'). And even among tumor cells, a segment of the genome may not be characterized by an integer copy number, due to tumor heterogeneity.

Consequently, it is useful to relax the assumptions that constrain the coverage levels of the states of the model, allowing the ratios of coverage to be continuously valued. This increases the challenge of finding the correct values and also introduces the problem of deciding how many states to include, leading the analysis to include a model selection component. Consequently, the goal of the analysis is modified to be to segment the genome into regions of uniform 'abundance class', without forcing an interpretation of a given class as being an integer copy number.

In theory, the HMM could simply be fit with varying numbers of states, using EM to determine the expected coverage level for each state, and choose the number of states that gives the best fit. In practice, unconstrained estimation of model parameters for any given number of states is not a robust process. Consequently, to address this, in another aspect an additional initial step or module is introduced that estimates the number of states and their means based on the overall coverage distribution, and another step is introduced which optimizes an initial model by sequentially adding states to the model and then sequentially removing states from the model.

Initial Model Generation:

The distribution of (corrected, normalized, window-averaged) coverage over the whole genome to be segmented is a mixture of the distributions of the different abundance classes. One approach to identifying distinct abundance classes is to look for peaks in the smoothed whole genome coverage distribution. (In another embodiment, another approach is to identify a mixture model which closely fits the observed coverage distribution.) An improvement over direct identification of peaks is realized by applying the quantile function for a normal distribution to the cumulative distribution function (cdf), and then take the difference between successive values, prior to smoothing and peak detection. This latter approach gives better sensitivity to identifying small peaks outside the central abundance classes.

For example, given a histogram of coverage $H=h_0, h_1, h_2, \ldots H_n$ where $h_i$ is the number of positions with coverage i and n is the smallest value such that less than 0.001 of the full histogram is truncated, and letting Q(p) be the quantile function for a normal distribution, the resulting peak locations, P, can be computed as follows:

$$N=\Sigma_{i=0}^{i=n} h_i$$

$$c_i=h_i/N$$

$$q_i=Q(c_i)$$

$$d_i=q_i-q_{i-1}$$

$$D=d_1, d_2, \ldots, d_n$$

$$S=\text{smooth}(D)$$

$$s_i=S(i)$$

$$m(i) = \begin{cases} 1 & \text{if } s_i > s_{i-1} \text{ and } s_i > s_{i+1} \text{ and for } i \text{ an integer} \\ 0 & \text{otherwise} \end{cases}$$

$$P=\{i | m_i=1 \text{ and } d_i>0.002\}$$

The resulting peak locations, P, are used as states in an initial model, with expected coverage values equal to the center of each peak. The variances may be estimated using EM (the same constrained model fitting as described above in connection with normal sample segmentation).

Model Refinement:

In a further embodiment, once an initial model has been inferred in this fashion, the model is iteratively refined. First, additional states are evaluated. The addition of a state is evaluated between each successive pair of states (abundance classes, ordered by expected coverage), accepting the addition if the improvement in likelihood (Pr(data|model)) exceeds some threshold. That is, between each successive pair of states i and j with expected coverage $c_i$ and $c_j$, an attempt is made to add a state i' with initial coverage $c_{i'}(c_i+c_j)/2$. The $c_{i'}$ is optimized using EM, holding the expected coverage levels of all other (pre-existing) states fixed. If the optimization results in a value outside the interval $(c_i,c_j)$, or if the reduction Pr(data|model) does not exceed an acceptance threshold, the addition is rejected; otherwise, the addition is accepted. If an addition is accepted, addition of a further state between i and i' is attempted, with recursion until the further addition is not accepted. Once addition between all pairs of successive states is rejected, the addition process is terminated. Second, removal of states is evaluated. States are removed from the model one at a time and the resulting model is optimized using EM; if the resulting model is not sufficiently worse than the previous model, then the state removal is accepted.

In certain embodiments, the segmentation further comprises generation of an initial model that estimates the number of states and their means based on the overall coverage distribution. In certain embodiments, the method includes optimization of an initial model by various means known to those versed in modeling of quantitative data, including modifications to the number of states in the model as well as optimization of the parameters of each state. For example, modifications to the number of states in the model can be performed by sequentially adding states to the model and then sequentially removing states, or a combination of the two; similar procedures are employed in model selection methods used in multivariate regression. Optimization of the parameters of each state may be performed by estimation-maximization or many other approaches to optimizing a multivariate model.

Variations on the preceding process are well-known to those of skill in the art. For example, one might try removing each state from the maximal model to determine which has the least impact, remove that state and recurse. Such alternatives will be known to those versed in approaches to multivariate model selection. In another example, modifications to the number of states in the model can be performed by sequentially adding states to the model and then sequentially removing states, or a combination of the two; similar procedures are employed in model selection methods used in multivariate regression. Optimization of the parameters of each state may be performed by estimation-maximization or many other approaches to optimizing a multivariate model.

Segmentation and Segment Scoring:

Once the model is selected and parameters optimized, segmentation and segment scoring are determined as described for normal samples. In brief, continuous segments of positions with the same most-likely state are reported, with scores indicating the average over positions in the segment of the probability of a classification error.

The instant disclosure differs from many known approaches in that the key difference is that in place of intensity measurements at a large but specific set of locations on the genome (e.g. microarray data), the described approach is relevant to sequencing-based coverage depth measurements at every position on the genome (e.g. next gen sequencing data). Some of the additional differences are as follows:

1) Use of fractional counts for measuring coverage. In yet another embodiment, when a paired read (e.g., corresponding to a full DNB) maps to more than one location, measures of confidence are used to fractionally attribute the mapping to each location. The consequence is that this allows for assessing coverage in segmental duplications to a greater degree than other approaches.

2) One of the described approaches to correcting coverage bias. In yet another embodiment, the approach that weights each DNB (one specific implementation being to use logistic regression) provides the ability model the impact of multiple biasing factors, arguably giving better bias correction than previous approaches.

3) The use of estimates of copy number in each of the baseline/matched samples. In yet another embodiment, by estimating the copy number of each sample in a general baseline, or in a matched baseline, one of the challenges for previous methods, which involves the computation of relative intensity (microarrays) or relative coverage (sequencing-based CNV)), is avoided, namely the fact that the sample(s) used as the baseline can themselves have CNVs. When a baseline sample has a CNV, the intensity/coverage measured within the CNV locus will not provide an estimate of the intensity for the normal (typically diploid) copy number, leading the relative coverage of the sample of interest to have a different relationship to absolute copy number than in most of the genome. By adjusting the baseline samples themselves according to estimates of copy number, an expected linear relationship is preserved between copy number and relative coverage, allowing to more accurately infer absolute copy number.

4) Within the HMM, two features are distinctive. In yet another embodiment, these features permit more robust modeling of the data (more accurate CNV calling):

a) the methods by which the mean of each state is determined; these methods provide an alternative to using the usual HMM training methods (EM), which do not seem to reliably converge on useful values.

i) for normal samples, the median of the coverage in the expected-diploid portion of the sample is used to determine the mean of the diploid state, and fix other states (copy numbers) at 50% increments or decrements from the diploid state. (The 0-copy state is special, being given a value slightly above 0 to allow for mis-mapping.)

ii) for tumor samples, a separate process is used to infer an initial set of levels; this process can be based on analysis of a histogram of coverage data; once initial levels are chosen, further calculations are applied to refine the set of levels.

b) the methods by which the variances of the states are estimated (constraint); at least in some implementations, the variances are constraint to be linearly related to the means of the states, reflecting the fact that most of the variance is a result of bias rather than sampling noise; thus, within a given sample, a state (coverage level) with twice the mean as a second state will typically have twice the spread (standard deviation) of observed coverages as the second state.

5) The use of coverage data from a large (e.g. 50 sample) baseline to determine locations where some aspect of the sequencing process leads to highly variable coverage levels. In yet another embodiment, such locations would lead to spurious CNV calls if they are not identified as problematic. Once identified, such locations are marked as of unknown copy number rather than being assigned spurious changes.

Window Boundary Definition (for Performing Window-Smoothing)

When choosing window boundaries for performing window-smoothing, in an example embodiment, for the most part windows are defined so that their chromosome coordinates are even multiples of the window length, so that for 2k windows, e.g., the chromosome positions of window boundaries will end with 'x000', where x is an even digit. The boundaries of these windows are called the 'default boundaries'. Exceptions to these default boundaries will be windows at the ends of contigs. Windows will never span bases taken from more than one contig, even if the gap between contigs is small enough to permit this. Moreover, there will be special treatment of the bases outside the outermost full default windows for each contig. These 'outside bases' will either be added to the first full window towards the center of the contig or be placed in their own window, depending on whether the number of bases is larger than $\frac{1}{2}$ the window width or not. For example, for a contig running from position 17891 to position 25336, and window width of 2000, the following list of window intervals may be used (17891,20000), (20000,22000), (22000,24000), (24000,25336)

It is noted that the first 109 bases of the contig are added to the 2k interval immediately to their right, while the last 1336 bases are placed in their own window. A contig that is smaller than the window width (e.g., chrM for 100k windows) will be made into a single window that includes the entire contig. No windows will be reported for inter-contig gaps. To illustrate, suppose a chromosome consists of three contigs as illustrated in Table 1.

TABLE 1

Chromosome contigs example

| Contig Id | Begin position | End position |
|---|---|---|
| 1 | 17891 | 25336 |
| 2 | 25836 | 29277 |
| 3 | 33634 | 34211 |

This would result in the following windows being used/reported; contig Id is shown only for clarity of presentation here:

Contig 1: (17891,20000), (20000,22000), (22000,24000), (24000,25336)
Contig 2: (25836,2800), (28000,29277)
Contig 3: (33634,34211)

The Consequences of this approach are:
all non-gap bases of the genome are included in a window (and only one window);
windows are restricted to a single contig;
windows are between 0.5 and 1.5 times the nominal window width;
window boundaries are mostly round numbers, making it more obvious that segment boundaries correspond to window boundaries, with less chance of over-interpreting the precision of the CNV call boundaries.

5. Population-Based No-Calling/Identification of Low-Confidence Regions

In various embodiments, the computations and steps described in this section (Section 5) can be performed by computer logic such as, for example, CNV variant caller 18 in FIG. 1 and/or by a component thereof such as population-based no-calling logic 38.

In one aspect, the HMM-based calls described above typically contain a variety of inferred CNVs that are either artifacts or of lesser interest. Primarily, these arise in one of two situations: A) The reference genome sequence does not provide an explanation for coverage patterns in most or all sample genomes, with most or all sample genomes matching one another. B) There is more variation in coverage than can be explained by a small number of discrete ploidy levels. The utility of CNV inference may be increased by identifying and annotating such regions. Below, regions so-annotated are considered to be 'no-called' in the sense that a discrete estimate of ploidy may not be given for these regions.

Such behaviors may result from multiple causes; some of the possible mechanisms include:

Errors in the reference genome. For instance, two contigs may in fact overlap one another, i.e. correspond to a single genomic interval, in most or all genomes. In this case, the two contig ends may consist in part of highly similar sequence that is otherwise unique, causing DNBs to map to both locations. Observed/measured coverage will be reduced, leading to an apparent copy number reduction. Alternatively, most or all sample genomes may contain a duplication that is not present in the reference. In this case, observed coverage will be elevated over the portion of the reference corresponding to the duplicated segment, leading to a copy number increase relative to the reference but not a true polymorphism.

Uncorrected coverage bias. In one aspect, a region that is substantially over or under represented in the sequencing results may appear to be a CNV relative to the reference. In order to retain the ability to make absolute copy number inferences, baseline correction as described above is done taking into account an initial copy number inference for the baseline genome(s). A consequence of this may be that regions that are severely biased in the baseline as well as the sample of interest may be interpreted as true CNVs. The signature of this sort of event will be that most or all samples will show similar elevated or suppressed coverage patterns.

Analysis artifacts. Though rare, there are occasional mapping artifacts that can result in a large number of spurious mappings at a given location. Such artifacts may result from particular arrangements of variations from the reference in repeated segments, such that the wrong reference copy of a repeat is more similar to the sequence of the sample of interest. These can result in a very substantial spike in coverage at certain locations on the reference, in a manner that is dependent on the variations present in a given sample.

Segmental duplications and tandem repeats. A segment that is present in duplicated form in the reference and subject to population variation may result in changes in coverage among samples that are smaller than typical of a copy number gain or loss in unique sequence. In the limit, sufficient variability in the population regarding a high-copy sequence type may result in an essentially continuous range of coverage values across a large number of samples.

Unstable estimation due to extreme correction factors or very low raw coverage. Examples include: 1) regions where coverage is very low due to GC correction, and the GC correction factors are correspondingly large, so that noise in the coverage estimate is amplified by the correction factors; 2) regions where coverage is very low due to mapping overflow, in simulations as well as real data, leading to large correction terms in the baseline bias correction factors; 3) regions where nearly all baseline genomes have ploidy 0.

Identification of such regions could be conducted in various ways. Ultimately, manual curation of coverage patterns at individual locations may be highly effective, but may be prohibitive in some circumstances due to lack of data, degree of effort, and/or process instability. Use of sequence similarity and/or structural annotations has some promise, as a large fraction of problematic regions in practice correspond to known repetitive portions of the reference genome (segmental duplications, self-chains, STRs, repeat-masker elements); however, since many real copy number polymorphisms occur in such regions, it is unappealing to overly-broadly exclude such segments and challenging to find criteria that are more selective. Thus, in yet another aspect, it is desirable to be able to identify problematic regions directly from coverage data.

Two sorts of coverage patterns typify several of the above circumstances. The first involves regions where coverage is more variable than can be explained by a small number of discrete ploidy levels ("hypervariable"). The second involves regions where coverage is not as expected of a euploid region matching the reference but it is similar among all samples ("invariant").

Given a substantial number of genomes (e.g. 50 or more), the "background set", summary statistics on bias-corrected and smoothed but unnormalized coverage data are sufficient to usefully (if heuristically/imperfectly) separate the genome into well-behaved regions, hypervariable regions and invariant regions. The following summary statistics computed for every genomic position i over a set G of n genomes can be used in this way. Let $\bar{c}'_{i<x>}$ for $1 \leq x \leq n$ be the x'th order statistic of $\bar{c}_i'(g)$, $g \in G$, i.e. the x'th smallest corrected and smoothed coverage at position i among the genomes in the background set.

Median $\tilde{m}_i$:

$$\tilde{m}_i = \begin{cases} \bar{c}'_{i(\frac{n+1}{2})} & \text{for } n \text{ odd} \\ \frac{(\bar{c}'_{i((n/2)} + \bar{c}'_{i(n/2+1)})}{2} & \text{for } n \text{ even} \end{cases}$$

Spread $s_i$:

$$s_i = \bar{c}'_{i<n>} - \bar{c}'_{i<1>} = \max_{g \in G} \bar{c}_i'(g) - \min_{g \in G} \bar{c}_i'(g)$$

Clustering coefficient $q_i$:

$$q_i = \frac{\min_{1 \leq q < r < s \leq n} SSE(i, 0, q) + SSE(i, q, r) + SSE(i, r, s) + SSE(i, s, n)}{SSE(i, 0, n)}$$

where $SSE(i, x, y)$ is the sum of squared error for $\bar{c}'_{i<x+1>}, \ldots, \bar{c}'_{i<y>}$, i.e. for $$C_{i,x,y} = \Sigma_{x < t \leq y}(\bar{c}'_{i<x+1>}, \ldots, \bar{c}'_{i<y>})/(y-x)$$

$$SSE(i,x,y) = \Sigma_{x < t \leq y}(\bar{c}'_{i<t>} - C_{i,x,y})^2$$

Given these summary statistics, criteria may be defined for labeling positions as hypervariable or invariant.

Annotation of Hypervariable Regions

A position that satisfies all of the following four criteria may be labeled "hypervariable" (rather than being marked as a CNV or classified as euploid):

(i) The position would be called a CNV/aneuploid by the HMM inference process described above.

(ii) Coverage values in the background set are not clustered in ways suggesting simple polymorphism in the population. Formally, for Q a value that can be chosen empirically as described below:

$q_i > Q$ (iii) The range of coverage values at this position in the background set is wider than is seen at most of the (euploid) genome. Formally, for S a value that can be chosen empirically as described below:

$s_i/\tilde{m}_i > S$ (iv) The observed coverage for the sample of interest falls within the range of values seen in the background set, or outside the observed range by a small absolute amount (e.g. an amount that could readily be explained by sampling or process variation). Formally, for R and X values that can be chosen empirically as described below:

$|\bar{c}_i' - \tilde{m}_i| < \min(s_i * R, X)$

Annotation of Invariant Regions

A position that satisfies all of the following criteria may be labeled "invariant" (rather than being marked as a CNV):

(i) The position would be called a CNV/aneuploid by the HMM segmentation process described above.

(ii) Coverage values in the background set are not clustered in ways suggesting simple polymorphism in the population. Formally, for Q a value that can be chosen empirically as described below:

$q_i > Q$ (iii) Coverage at this position across the background samples shows low variability, suggesting both absence of a high-minor-allele-frequency polymorphism in the population and low process variation (artifact). Formally, for S a value that can be chosen empirically as described below:

$s_i/\tilde{m}_i < S$ (iv) The observed coverage for the sample of interest falls within the range of values seen in the background set, or outside the background range by a small absolute amount (e.g. an amount that could readily be explained by sampling or process variation). Formally, for R and X values that can be chosen empirically as described below:

$|\bar{c}_i' - \tilde{m}_i| < \min(s_i * R)$

Refinement of Annotations

In one aspect, the above criteria may cause CNV calls to be overly fragmented into alternating called and no-called segments. It may be desirable to permit short intervals that would be "no-called" (i.e. annotated as "hypervariable" or "invariant") based on the criteria above to be allowed to be called (left unannotated) if the observed coverage is sufficiently similar to a flanking interval that is not annotated. Concretely, the "hypervariable" or "invariant" labeling of intervals, which are less than L bases that satisfy the above criteria but are part of longer segments in the HMM output, may be suppressed.

Selection of Cutoff Values

In one aspect, cutoffs Q, S, R, X and L in the above criteria may be selected based on analysis of a subset of initial CNV calls and comparison to genome-wide distributions on the background coverage summary statistics. Given a classification of an initial set of CNV calls (the "training set") into those that are suspect (to be labeled "hypervariable" or "invariant") and those that are believed to be true CNVs, as well as summary statistics for the entire genome (that is, of selected positions spaced along the genome, e.g. those resulting from the windows described above), the cutoffs that are near optimal may be identified with regard to the following criteria:

- most of the genome is called either euploid or CNV/aneuploid (e.g., only a small fraction of the genome is no-called/annotated as hypervariable or invariant);
- most of the problematic regions in the 'training set' are no-called;
- most of the trusted regions in the training set are called (not annotated).

The training set can be derived based on manual curation of a collection of preliminary CNV calls. Said curation may involve manual inspection of coverage profiles to identify calls and comparison to external datasets of putative CNVs identified by independent means.

Candidate values of Q, R, S and L may be evaluated by determining concordance with the training set or a separate test set, as well as the fraction of the genome that is no-called. The final choice of cutoffs may involve a tradeoff between completeness of calling (fraction of the genome called) and the amount of problematic CNV calling.

Score Computation

The CNV segmentation scores described above are more explicitly described in this section.

The probability of a given sequence $D=d_1,\ldots,d_t$ of outputs of length t occurring as the result of a specific sequence of states $\sigma=s_1,\ldots,s_t$ can be computed on a given HMM consisting of n states defined by initial state probabilities $P=p_1,\ldots p_n$, transition probabilities $T=\{t_{ij}\}$ and emission probabilities $E=\{e_{sd}\}$ as follows:

$$Pr(D, \sigma \mid P, T, E) = p_{s_1} * e_{s_1,d_1} * \sum_{i=2}^{t} t_{s_{i-1},s_i} e_{s_i,d_i}$$

The probability of the data given the model is the sum over all possible sequences of states, i.e. for S the set of all possible sequences of states of length t:

$$Pr(D \mid P,T,E) = \Sigma_{\sigma \in S} Pr(D,\sigma \mid P,T,E)$$

This and other equations involving sums over subsets of S can be efficiently computed using the Forward/Backward algorithm. Application of Bayes' Rule allows the determination of the probability of a given path given the data and the model:

$$Pr(\sigma \mid P, T, E, D) = \frac{Pr(D, \sigma \mid P, T, E)}{Pr(D \mid P, T, E)}$$

From this, it can be seen that the most probable path, given the data and model, is the path which maximizes $Pr(D,\sigma \mid P, T, E)$. The path which maximizes this equation can efficiently be determined using the Viterbi algorithm.

However, the probability of partial paths can also be computed. For example, the probability the path through the model that actually led to an observed sequence of data was in a particular state q at a particular time u can be computed as follows:

$$Pr(s_u = q \mid P, T, E, D) = \frac{Pr(D, s_u = q \mid P, T, E,)}{Pr(D \mid P, T, E)}$$

The denominator is discussed above, and the numerator can be obtained by summing the probability of the data and a particular path over all paths for which $s_u=q$, denoted $S_{s_u=q}$:

$$Pr(D, s_u = q \mid P, T, E) = \sum_{\sigma \in S_{s_u=q}}^{t} Pr(D, \sigma \mid P, T, E)$$

Thus:

$$Pr(s_u = q \mid P, T, E, D) = \frac{\sum_{\sigma \in S_{s_u=q}} Pr(D, \sigma \mid P, T, E)}{\sum_{\sigma \in S} Pr(D, \sigma \mid P, T, E)}$$

State assignment ("called ploidy") is done as follows; the state (ploidy) inferred at position u, $\hat{s}_u$ is that state with maximal probability:

$$\hat{s}_u = \operatorname{argmax}_q Pr(s_u = q \mid P,T,E,D)$$

(In case of a tie, choose arbitrarily.) The ploidyScore at position u, $\pi_u$ is then:

$$\pi_u = -10 * \log_{10}(1 - Pr(s_u = \hat{s}_u \mid P,T,E,D))$$

And the CNVTypeScore Score (also referred to as DEI Score) at position u, $\delta_u$, is:

$$\delta_u = -10 * \log_{10}(1 - \Sigma_{q=a}^{b} Pr(s_u = q \mid P,T,E,D))$$

The bounds on the summation, a and b, are as follows. For a region expected to be diploid, if $\hat{s}_u < 2$, a=0, b=1; if $\hat{s}_u < 2$, a=b=2; if $\hat{s}_u > 2$, a=3, b=maximum ploidy (typically, 10). For a region expected to be haploid (male sex chromosomes), if $\hat{s}_u < 1$, a=0, b=0; if $\hat{s}_u = 1$, a=b=1; if $\hat{s}_u > 1$, a=2, b=maximum ploidy (typically, 10).

A segment is defined as a maximal run of like-ploidy positions. For a segment from position l to position r, the ploidyScore $\pi_{l,r}$, is taken to be the mean of the ploidyScores for the constituent positions:

$$\pi_{l,r} = \frac{\sum_{u=l}^{r} \pi_u}{r - l + 1}$$

And similarly the CNVTypeScore of a segment, $\pi_{l,r}$, is the mean of the CNVTypeScores for the constituent positions:

$$\delta_{l,r} = \frac{\sum_{u=l}^{r} \delta_u}{r - l + 1}$$

An Alternative Approach For Scoring:

An alternative set of scores for segments can be computed based on the likelihoods of partial paths. For instance, the probability of the true path being in state q from position l to position r can be computed as follows:

$$Pr(s_l = s_{l+1} = \ldots = s_r = q \mid P, T, E, D) = \frac{\sum_{\sigma \in S_{s_l=s_{l+1}=\ldots=s_r=q}} Pr(D, \sigma \mid P, T, E)}{\sum_{\sigma \in S} Pr(D, \sigma \mid P, T, E)}$$

Another statistic that may be relevant to computing confidence in segment boundaries is the probability of being in state q at position u, but not at position u−1 (or, analogously, at position u+1):

$$Pr(s_u = q, s_{u-1} \neq q \mid P, T, E, D) = \frac{\sum_{\sigma \in S_{s_u=q, s_{u-1} \neq q}} Pr(D, \sigma \mid P, T, E)}{\sum_{\sigma \in S} Pr(D, \sigma \mid P, T, E)}$$

Finally, an alternative to the DEI Scores defined above can be computed; for example, the probability of being in states with ploidy greater than 2 from position l to position r is:

$$Pr(s_{i:l\leq i\leq r} > 2 \mid P, T, E, D) = \frac{\sum_{\sigma \in S_{s_{i:l\leq i\leq r}>2}} Pr(D, \sigma \mid P, T, E)}{\sum_{\sigma \in S} Pr(D, \sigma \mid P, T, E)}$$

As noted earlier, all the summations over paths can be efficiently computed via the Forward-Backward algorithm.

Some HMM References:

Wikipedia:

HMMs http://en.wikipedia.org/wiki/Hidden_Markov_model

Baum-Welch http://en.wikipedia.org/wiki/Baum%E2%80%93Welch_algorithm

Forward-Backward http://en.wikipedia.org/wiki/Forward-backward_algorithm

Viterbi algorithm http://en.wikipedia.org/wiki/Viterbi_algorithm

Figure 3:
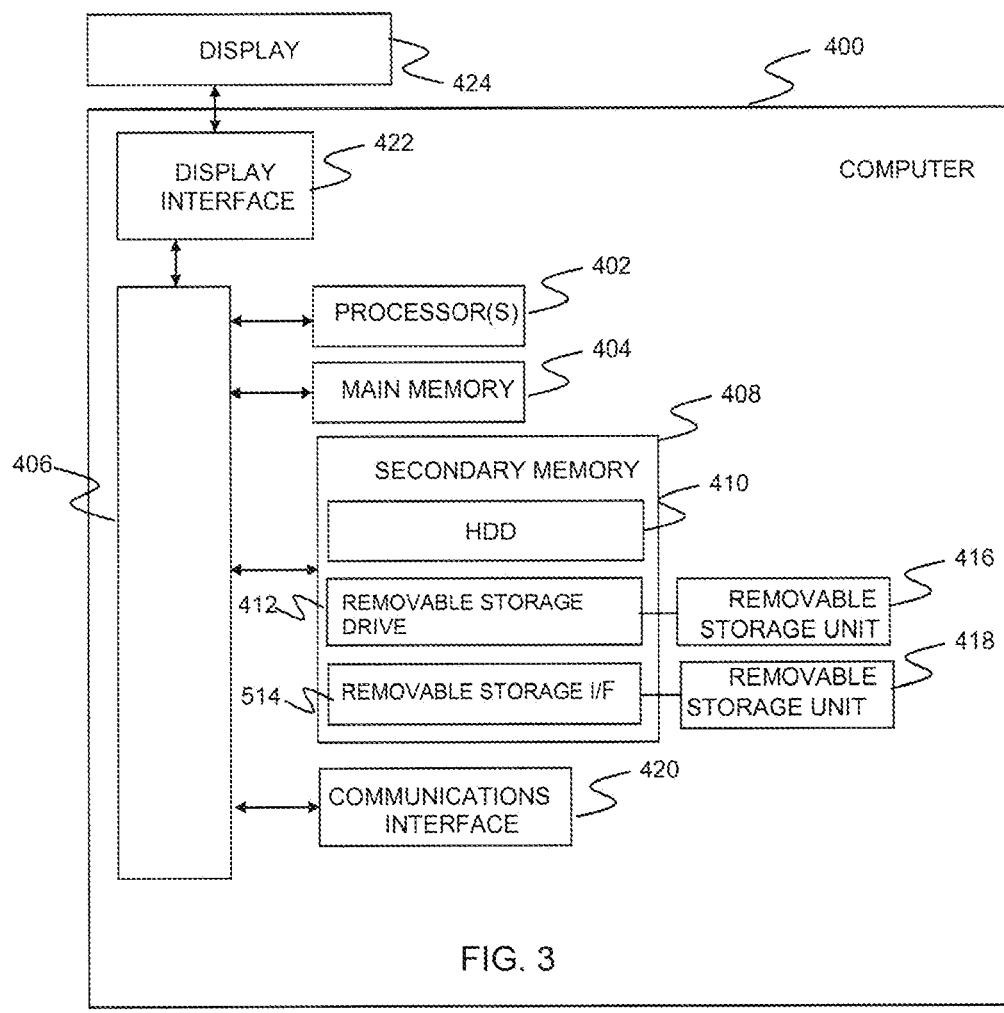
FIG. 3 depicts a generalized computer system incorporating and operative according to certain aspects of the instant disclosure.

A classic review: Rabiner, L. R. A Tutorial on Hidden Markov Models and Selected Applications in Speech Recognition. Proceedings of the IEEE, 1989, 77.2:257-286: http://www.ece.ucsb.edu/Faculty/Rabiner/ece259/Reprints/tutorial %20on%20hmm%20and% 20applications.pdf Exemplary Implementation Mechanisms for CNV Calling Computer System An exemplary computer system which can be used in accordance with the embodiments of the instant disclosure can be implemented in software and the results may be presented to a user on a monitor or other display device. In some embodiments, the exemplary computer system configured to estimate copy number variation in a target sequence in a sample can present results to a user as a graphical user interface (GUI) on a display device such as a computer monitor. FIG. 3 illustrates one example of an architecture of a computer system 400 configured to implement the estimate of copy number variation in accordance with the present disclosure. As illustrated in FIG. 3, computer system 400 may include one or more processors 402 (e.g., such as CPUs). The processor 402 is connected to a communication infrastructure 406 (e.g., a communications bus, cross-over bar, or network). Computer system 400 may include a display interface 422 that forwards graphics, text, and other data from the communication infrastructure 406 (or from a frame buffer not shown) for display on the display unit 424.

Computer system 400 also includes a main memory 404, such as a random access memory (RAM), and a secondary memory 408. The secondary memory 408 may include, for example, a hard disk drive (HDD) 410 and/or removable storage drive 412, which may represent a floppy disk drive, a magnetic tape drive, an optical disk drive, or the like. The removable storage drive 412 reads from and/or writes to a removable storage unit 416. Removable storage unit 416 may be a floppy disk, magnetic tape, optical disk, or the like. As will be understood, the removable storage unit 416 may include a computer readable storage medium having stored therein computer software and/or data.

In alternative embodiments, secondary memory 408 may include other similar devices for allowing computer programs, computer logic, or other instructions to be loaded into computer system 400. Secondary memory 408 may include a removable storage unit 418 and a corresponding interface 514. Examples of such removable storage units include, but are not limited to, USB or flash drives, which allow software and data to be transferred from the removable storage unit 418 to computer system 400.

Computer system 400 may also include a communications interface 420. Communications interface 420 allows software and data to be transferred between computer system 400 and external devices. Examples of communications interface 420 may include a modem, Ethernet card, wireless network card, a Personal Computer Memory Card International Association (PCMCIA) slot and card, or the like. Software and data transferred via communications interface 420 may be in the form of signals, which may be electronic, electromagnetic, optical, or the like that are capable of being received by communications interface 420. These signals may be provided to communications interface 420 via a communications path (e.g., channel), which may be implemented using wire, cable, fiber optics, a telephone line, a cellular link, a radio frequency (RF) link and other communication channels.

In this document, the terms "computer-program medium" and "computer-readable storage medium" refer to non-transitory media such as main memory 404, removable storage drive 412, and a hard disk installed in hard disk drive 410. These computer program products provide software or other logic to computer system 400. Computer programs (also referred to as computer control logic) are stored in main memory 404 and/or secondary memory 408. Computer programs or other software logic may also be received via communications interface 420. Such computer programs or logic, when executed by a processor, enable the computer system 400 to perform the features of the method discussed herein. For example, main memory 404, secondary memory 408, or removable storage units 416 or 418 may be encoded with computer program code (instructions) for performing operations corresponding to the process shown in FIG. 3.

In an embodiment implemented using software logic, the software instructions may be stored in a computer program product and loaded into computer system 400 using removable storage drive 412, hard drive 410, or communications interface 420. In other words, the computer program product, which may be a computer readable storage medium, may have instructions tangibly embodied thereon. The software instructions, when executed by a processor 402, cause the processor 402 to perform the functions of (operations of) methods described herein. In another embodiment, the method may be implemented primarily in hardware using, for example, hardware components such as a digital signal processor comprising application specific integrated circuits (ASICs). In yet another embodiment, the method is implemented using a combination of both hardware and software.

Exemplary system for CNV calling in accordance with an embodiment of the present disclosure.

FIG. 1 is a block diagram illustrating a system for calling variations in a sample polynucleotide sequence according to one exemplary embodiment. In this embodiment, the system may include a computer cluster 10 of one or more computing devices such as computers 12 and a data repository 14. The computers 12 may be connected to the data repository 14 via a high-speed local area network (LAN) 16. At least a portion of the computers 12 may execute instances of a CNV caller 18. (In some embodiments, a CNV caller such as CNV caller 18 may be included as part of an assembly pipeline logic that is configured and operable to assemble raw reads into mapped and sequenced genomes that include the detected variations from a reference genome; examples of such embodiments are described in U.S. application Ser. No. 12/770,089 filed on Apr. 29, 2010, the entire contents of which are hereby incorporated by reference as if fully set forth herein.) The CNV caller 18 may include HMM model logic 20, coverage calculation logic 22, GC correction logic 34, ploidy-aware correction logic 36, and population-based no-calling logic 38.

The data repository 14 may store several databases including one or more databases that store a reference polynucleotide sequence 24, mated reads 26 obtained by sequencing a sample polynucleotide sequence using biochemical processes, and mapped mated reads 28 that are generated from the mated reads 26.

The reference polynucleotide sequence 24 (hereinafter referred to as simply the reference) refers to a known sequence of nucleotides of a reference organism (e.g., a known genome). This includes references comprising sequences having known variations at one or more location within the genome. A polynucleotide molecule is an organic polymer molecule composed of nucleotide monomers covalently bonded in a chain. Deoxyribonucleic acid (DNA) and ribonucleic acid (RNA) are examples of polynucleotides with distinct biological function. The genome of an organism (e.g., such as a human) is the entirety (or the substantial entirety) of an organism's hereditary information, which is encoded as DNA or RNA. A haploid genome contains one copy of each hereditary unit of the organism. In diploid organisms such as mammals, the genome is a series of complementary polynucleotides comprising two copies of the majority of the hereditary information organized as sets of chromosomes having discrete genetic units, or alleles. Each copy of the allele is provided at a specific position on an individual chromosome, and the genotype for each allele in a genome comprises the pair of alleles present at particular positions on homologous chromosomes that determine a specific characteristic or trait. Where a genome comprises two identical copies of an allele it is homozygous for that allele, and when the genome comprises two different alleles it is heterozygous for that locus. The DNA itself is organized as two strands of complementary polynucleotides.

The reference 24 may be an entire genome sequence, a portion of a reference genome, a consensus sequence of many reference organisms, a compilation sequence based on different components of different organisms, or any other appropriate sequence. The reference 24 may also include information regarding variations of the reference known to be found in a population of organisms.

The mated reads 26 may be obtained during a sequencing process performed on polynucleotide sequences derived from a biological sample of an organism, e.g., nucleic acid sequences from a gene, genomic DNA, RNA, or fragments thereof, that is to be analyzed. The mated reads 26 can be obtained from a sample comprising an entire genome, such as an entire mammalian genome, more specifically an entire human genome. In another embodiment, the mated reads 26 may be specific fragments from a complete genome. In one embodiment, the mated reads 26 may be obtained by performing sequencing on amplified nucleic acid constructs, such as amplimers created using polymerase chain reaction (PCR) or rolling circle replication. Examples of amplimers that may be used are described, for example, in U.S. Pat. Publication Nos. 20090111705, 20090111706 and 20090075343, which are incorporated by reference in their entirety.

The mapped mated reads 28 refer to the mated reads 26 that have been mapped to locations in the reference 24. Exemplary mapping methods are described in the following patent applications: U.S. patent application Ser. No. 12/698,965 filed on Feb. 2, 2010, the entire contents of which is hereby incorporated by reference; U.S. patent application Ser. No. 12/698,986 filed on Feb. 2, 2010, the entire contents of which is hereby incorporated by reference; U.S. patent application Ser. No. 12/698,994 filed on Feb. 2, 2010, the entire contents of which is hereby incorporated by reference.

The copy number variation CNV caller 18 generates and scores sequences for the purpose of identifying and calling the copy number variations or differences detected in a sequence of the mapped mated reads 28 in relation to the reference 24.

The CNV caller 18 may output a CNV calls file(s) 32, list or other data structure containing the identified variations, each describing a manner in which parts of the sequence of mapped mated reads 28 are observed to differ from the reference 24 at or near specific locations.

The computer cluster 10 may be configured such that instances of the CNV caller 18 executing on different computers 12 operate on different portions of the reference 24 and the mapped mated reads 26 in parallel. The job scheduler 30 is responsible for assignment of jobs or packets of work across the various computers 12 in the computer cluster 10.

The computers 12 may include typical hardware components (not shown) including, one or more processors, input devices (e.g., keyboard, pointing device, etc.), and output devices (e.g., a display device and the like). One example of a computer 12 is computer system 400 illustrated in FIG. 3. The computers 12 may include computer-readable/writable media, e.g., memory and storage devices (e.g., flash memory, a hard drive, an optical disk drive, a magnetic disk drive, and the like) containing computer instructions that implement the functionality disclosed when executed by the processor. The computers 12 may further include computer writeable media for implementing the data repository 14 and for storing the CNV call file(s) 32. The computers 12 may further include wired or wireless network communication interfaces for communication.

Data Generation

In some embodiments, a sequencing machine may be used to generate the mated reads 26 obtained from the sample polynucleotides of an organism to be analyzed. In one embodiment, the sequencing machine provides the data in discrete but related sets, such that contents of the mated reads 26 may include predicted spatial relationships and/or separation variations. The relationships may be determined based on existing knowledge about the biochemical process used to generate the mated reads 26 (e.g., based on sequences that would be expected to be obtained if the biochemical process were applied to a sample), empirical estimates based on preliminary analysis of the sequence data of the mated reads 26 or subsets thereof, estimation by experts, or other appropriate techniques.

Numerous biochemical processes can be used to facilitate the generation, by a sequencing machine, of the mated reads 26 for use with the present CNV calling methods. These include, but are not limited to hybridization methods as disclosed in U.S. Pat. Nos. 6,864,052; 6,309,824; 6,401,267; sequencing-by-synthesis methods as disclosed in U.S. Pat. Nos. 6,210,891; 6,828,100, 6,833,246; 6,911,345; 7,329,496 and Margulies, et al. (2005), *Nature* 437:376-380 and Ronaghi, et al. (1996), *Anal. Biochem.* 242:84-89; ligation-based methods as disclosed in U.S. Pat. No. 6,306,597, WO2006073504, WO2007120208, nanopore sequencing technology as disclosed in U.S. Pat. Nos. 5,795,782, 6,015,714, 6,627,067, 7,238,485 and 7,258,838 and U.S. Pat Appln Nos. 2006003171 and 20090029477, and nanochannel sequencing technology as disclosed in US Pat. App. Pub. No. 20090111115, all of which are incorporated by reference in their entirety. In a specific implementation, a Combinatorial Probe Anchor Ligation (cPAL) process is used in some embodiments (see US Pat. App. Publication Nos. 20080234136 and 20070099208, which are incorporated herein by reference in their entirety).

Figure 2:
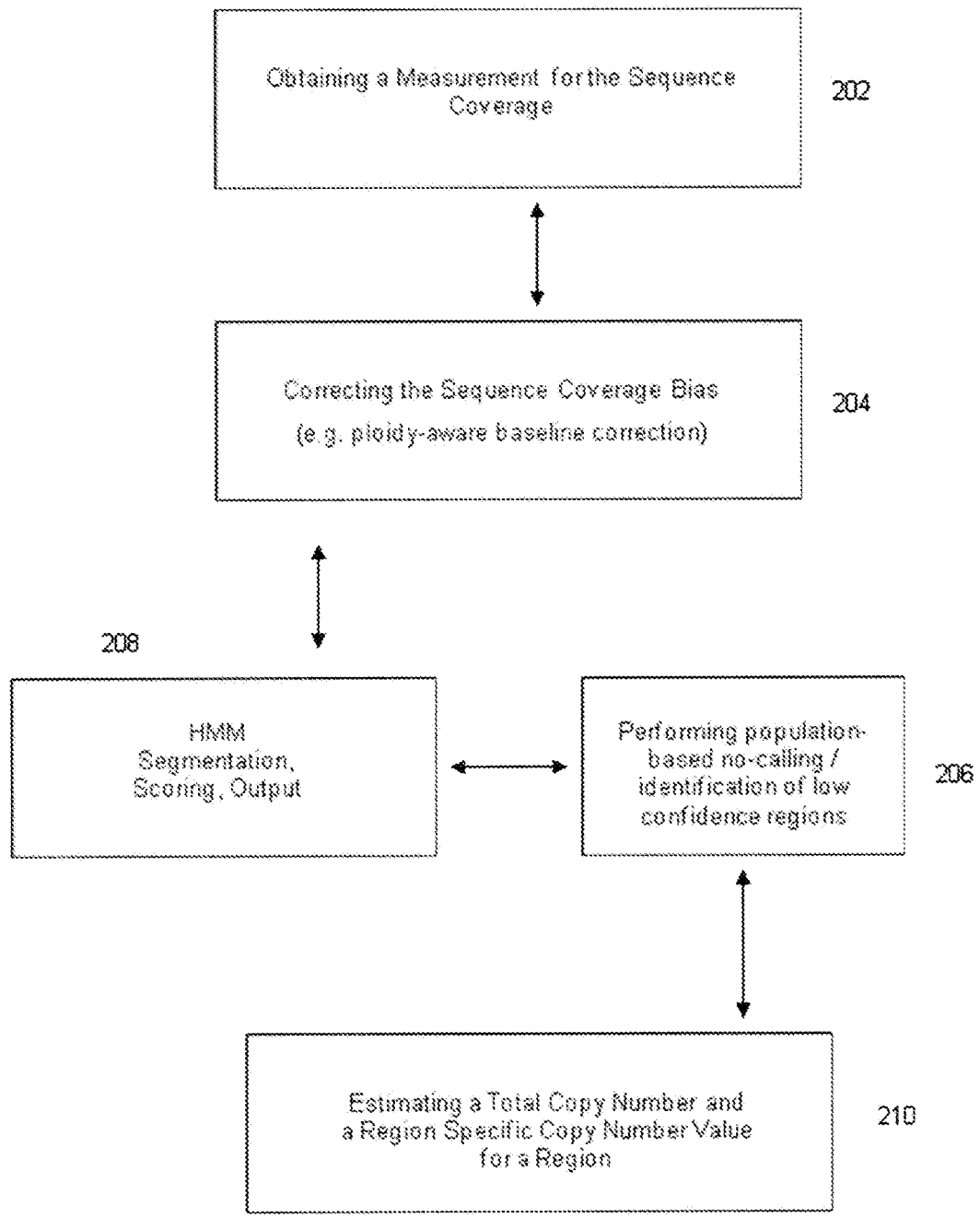
FIG. 2 depicts a generalized flow chart illustrating the CNV calling method according to an embodiment of the present disclosure.

Once the primary mapped mated read data is generated, the information is processed in accordance with the CNV calling methods of the instant disclosure as illustrated in FIG. 2, which depicts an exemplary method for determining the copy number of a genomic region at a detection position of a target polynucleotide sequence in a sample, mapped read data is obtained to measure the sequence coverage for said sample 202; the sequence coverage bias is corrected wherein the sequence coverage bias correction comprises performing ploidy-aware baseline correction 204; total copy number value and region-specific copy number value for a plurality of genomic regions are estimated 210 after population based no calling/identification of low confidence regions is performed 206 and HMM segmentation, scoring, and output is performed 208.

Examples of output of the CNV calling process (e.g., as may be provided in variation call file(s) 32 in FIG. 1) for diploid/non-tumor/non-aneuploid samples generated in accordance with an exemplary embodiment of the instant disclosure are illustrated in Table 2.

TABLE 2

Sample illustration of output of CNV calling process for diploid/non-tumor/non-aneuploid samples

| Chromosome | Begin | End | Ploidy | PloidyScore | Type | TypeScore |
|---|---|---|---|---|---|---|
| Chr1 | 10001 | 5100000 | 2 | 25 | = | 25 |
| Chr1 | 5100001 | 5800000 | 3 | 15 | + | 40 |
| Chr1 | 5800001 | 63428000 | 2 | 19 | = | 19 |
| Chr1 | 63428001 | 63518000 | N | 0 | hypervariable | 0 |
| Chr1 | 63518001 | 220000000 | 2 | 15 | = | 15 |
| Chr1 | 220000001 | 220006000 | 1 | 5 | − | 5 |
| Chr1 | 220006001 | 249240621 | 2 | 28 | = | 28 |
| Chr2 | 10001 | 534000 | N | 0 | hypervariable | 0 |
| Chr2 | 534001 | 9374000 | 2 | 16 | = | 16 |
| Chr2 | 9374000 | 9388000 | N | 0 | invariant | 0 |
| Chr2 | 9388001 | 17151000 | 2 | 13 | = | 13 |
| . . . | | | | | | |

In Table 2, column "Chromosome" identifies the chromosome number, columns "Begin" and "End" identify the starting and ending locus of a given region, column "Ploidy" indicates the ploidy (e.g., such as copy number) for a region, column "Ploidy Score" indicates a score for a given region (where the score is a logarithm-based value expressed in decibels dB), column "Type" indicates the type of the ploidy observed for a region (e.g., "=" indicates the normal ploidy of 2, "+" indicates ploidy higher than the normal, "−" indicates ploidy lower than normal, "hypervariable" indicates that the ploidy could not be called, and "invariant" indicates that the ploidy is different than normal but is the same as observed in a baseline that is a collection of at least several reference genomes), and column "TypeScore" indicates a confidence score for the type called in the same row in column "Type". For example, the second row in Table 2 indicates that: the region, beginning at locus 5100001 and ending at locus 5800000 on chromosome 1, has a ploidy of 3 that has a score of 15 dB and has an "increased" Type having a score of 40.

Examples of output of the CNV calling process output (e.g., as may be provided in variation call file(s) 32 in FIG. 1) for non-diploid/tumor/aneuploid samples generated in accordance with an exemplary embodiment of the instant disclosure are illustrated in Table 3.

TABLE 3

Sample illustration of output of CNV calling process for non-diploid/tumor/aneuploid samples

| Chromosome | Begin | End | Level | Level Score |
|---|---|---|---|---|
| Chr1 | 10001 | 249240621 | 1.05 | 57 |
| Chr2 | 10001 | 243189373 | 1.05 | 38 |
| Chr3 | 60001 | 148900000 | 0.68 | 81 |
| Chr3 | 148900001 | 149600000 | 1.45 | 7 |
| Chr3 | 149600001 | 197962430 | 1.05 | 66 |
| Chr4 | 10001 | 191044276 | 1.45 | 103 |
| . . . | | | | |

In Table 3, column "Chromosome" identifies the chromosome number, columns "Begin" and "End" identify the starting and ending locus of a given region, column "Level" indicates the coverage level for a region output by the HMM model (where the coverage level is computed without making the assumption of a normal ploidy of 2 because of the aneuploidy and other characteristics of the tumor sample), and column "LevelScore" indicates a confidence score for the level called in the same row in column "Level". For example, the second row in Table 3 indicates that: the region, beginning at locus 10001 and ending at locus 243189373 on chromosome 2, has a coverage level of 1.05 that has a score of 38.

While present invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention.

What is claimed is:

1. A method for determining copy number variation of a genomic region at a detection position of a target polynucleotide sequence in a sample, said method comprising:
   obtaining, using a computer, coverage values for each given position in a baseline or reference sample for the sequence coverage of said target polynucleotide using data generated from mate-pair mappings;

correcting, using the computer, the coverage values for each given position for sequence coverage bias, wherein correcting the coverage values for each given position in a baseline or reference sample comprises performing ploidy-aware baseline correction; and estimating, using the computer, a total copy number value and region-specific copy number value for each of a plurality of genomic regions based at least on the corrected coverage values for each given position in a baseline or reference sample.

2. The method of claim 1, wherein the method further comprises performing Hidden Markov Model (HMM) segmentation, scoring, and output based on the coverage values for each given position in a baseline or reference sample.

3. The method of claim 1, wherein the method further comprises performing population-based no-calling and identification of low-confidence regions.

4. The method of claim 1 wherein said method further comprises normalizing the coverage values for each given position in a baseline or reference sample for the sequence coverage by comparison to sequence data obtained from a baseline sample.

5. The method of claim 1 wherein obtaining the coverage values for each given position in a baseline or reference sample for the sequence coverage comprises measuring sequence coverage depth at every position of the genome.

6. The method of claim 1 wherein correcting the coverage values for each given position in a baseline or reference sample for the sequence coverage bias comprises calculating window-averaged coverage.

7. The method of claim 1 wherein correcting the coverage values for each given position in a baseline or reference sample for the sequence coverage bias comprises performing adjustments to account for GC bias in the nucleic acid templates generated from the sample during the library construction and/or sequencing process.

8. The method of claim 1 wherein correcting the coverage values for each given position in a baseline or reference sample for the sequence coverage bias comprises performing adjustments based on additional weighting factor associated with individual mappings to compensate for bias.

9. The method of claim 1 wherein the sequence coverage, $c_i$, is determined by $$c_i = \sum_{m \in M_i} P(DNB \mid R, m) \bigg/ \left( \propto + \sum_{n \in N(m)} P(DNB_m \mid R, n) \right).$$

10. The method of claim 1 wherein the sample-comprises at least one of:
a genome;
sequences of a plurality of approximately random fragments of a genome;
a reference genome; and
an assembled sequence whereby coverage values for each given position in a baseline or reference sample can be obtained as mapping data and/or coverage data.

11. The method of claim 2 wherein performing the HMM segmentation further comprises generating an initial model that estimates the number of states and their means based on the overall coverage distribution.

12. The method of claim 11 wherein performing the HMM segmentation comprises optimizing the initial model by performing one or more of modifying the number of states in the model and optimizing the parameters of each state.

13. The method of claim 11 wherein the corrected coverage at position i is:

$$c'_i = \sum_{m \in M_i} q_m * P(DNB \mid R, m) \bigg/ \left( \propto + \sum_{n \in N(m)} P(DNB_m \mid R, n) \right).$$

14. The method of claim 4 wherein normalizing the measurement data comprises determining normalized corrected coverage by using the equation:

$$\overline{c}''_i = \overline{c}'_i * \frac{\tilde{d}}{d'_i} * \frac{p_i}{2}.$$

15. The method of claim 1 further comprising using sequence coverage estimation to generate mappings of a sequenced fragment to more than one location on the genome, and using confidence measurements on each of the mappings to fractionally attribute said each mapping to each detection location.

16. The method of claim 1 further comprising performing HMM calculations to determine a ploidy number at each detection position.

17. The method of claim 1 further comprising performing HMM calculations to determine a ploidy score at each detection position, said ploidy score representing a confidence that the determined ploidy number at said detection position is correct.

18. The method of claim 1 further comprising performing HMM calculations to determine a CNV-Type-Score at each detection position, the CNV-Type-Score representing a confidence that said determined ploidy number at said detection position correctly indicates decreased ploidy, expected ploidy, or increased ploidy at said detection position.

19. The method of claim 2, wherein a plurality of states of the HMM correspond to respective copy numbers, and wherein if the sample is a normal sample, performing the HMM segmentation, scoring, and output includes:
initializing a mean of an emission distribution of the HMM for each state with copy number N greater than zero to N/2 multiplied by the median of the coverage in a portion of the sample expected to be diploid; and
initializing the mean of the emission distribution for the state with copy number 0 to a positive value smaller than that used for the state with copy number 1.

20. The method of claim 2, wherein plural states of the HMM correspond to respective copy numbers, and wherein if the sample is a tumor sample, performing the HMM segmentation, scoring, and output includes:
estimating the number of states and a mean of each state based on a distribution of the coverage to generate an initial model for the HMM;
optimizing the initial model by modifying the number of states in the model as well as optimizing the parameters of each state; and
modifying the number of states in the model by sequentially adding states to the model and then sequentially removing states, or a combination thereof.

21. The method of claim 20, wherein modifying the initial model comprises:
a) adding a new state between a pair of states if adding said new state improves a likelihood associated with the HMM beyond a first predetermined threshold;

b) repeating (a) recursively between each pair of states until no more additions are possible;

c) removing a state from the HMM if removal of said state does not decrease the likelihood beyond a second predetermined threshold; and d) repeating (c) iteratively for all the states.

22. The method of claim 2, wherein plural states of the HMM correspond to respective copy numbers, and wherein performing the HMM segmentation, scoring, and output includes initializing a variance of an emission distribution of the HMM for each state with copy number N to a constant multiplied by a mean of the emission distribution for said state.

23. The method of claim 10 wherein obtaining the coverage values for the sequence coverage comprises:

a) determining reads that represent the sequences of a plurality of approximately random fragments of the genome of the sample, wherein said plurality provides a sampling of the genome whereby on average a base position of the genome is sampled one or more times;

b) obtaining mapping data by mapping said reads to the reference genome, or by mapping said reads to an assembled sequence; and c) obtaining coverage data by measuring an intensity of sampled sequences along the reference genome or along the assembled sequence;

wherein the coverage values comprises the mapping data and the coverage data.

24. The method of claim 23 wherein determining the reads further comprises steps of:

a) providing a plurality of amplicons, wherein:

i) each amplicon comprises multiple copies of a fragment of the target polynucleotide sequence, ii) each amplicon comprises a plurality of interspersed adaptors at predetermined sites within the fragment, each adaptor comprising at least one anchor probe hybridization site, iii) said plurality of amplicons comprise fragments that substantially cover target nucleic acids in the sample;

b) providing a random array of said amplicons fixed to a surface at a density such that at least a majority of said amplicons are optically resolvable;

c) hybridizing one or more anchor probes to said random array;

d) hybridizing one or more sequencing probes to said random array to form perfectly matched duplexes between said one or more sequencing probes and fragments of target nucleic acid;

e) ligating the anchor probes to the sequencing probes;

f) identifying at least one nucleotide adjacent to at least one interspersed adaptor; and g) repeating steps (c) through (f) until a nucleotide sequence of said target nucleic acid is identified;

wherein steps (a)-(g) are performed by a sequencing machine.

25. A non-transitory computer-readable medium comprising instructions tangibly embodied thereon, the instructions when executed by a computer processor causing the processor to perform the operations of:

obtaining, using the processor, coverage values for each given position in a baseline or reference sample for the sequence coverage of said target polynucleotide using data generated from mate-pair mappings;

correcting, using the processor, the coverage values for each given position for sequence coverage bias, wherein correcting the coverage values for each given position in a baseline or reference sample comprises performing ploidy-aware baseline correction; and estimating, using the processor, a total copy number value and region-specific copy number value for each of a plurality of genomic regions based at least on the corrected coverage values for each given position in a baseline or reference sample.

26. A non-transitory computer-readable medium comprising instructions tangibly embodied thereon, the instructions when executed by a computer processor causing the processor to perform the operations of:

obtaining, using the processor, coverage values for each given position in a baseline or reference sample for the sequence coverage of said target polynucleotide using data generated from mate-pair mappings;

correcting, using the processor, the coverage values for each given position for sequence coverage bias, wherein correcting the coverage values for each given position in a baseline or reference sample comprises performing ploidy-aware baseline correction; and performing Hidden Markov Model (HMM) segmentation, scoring, and output based on the corrected coverage values for each given position in a baseline or reference sample;

based on the HMM scoring and output, performing population-based no-calling and identification of low-confidence regions; and based on the HMM scoring and output, estimating a total copy number value and region-specific copy number value for a plurality of regions.

27. A system of determining copy number variation of a genomic region at a detection position of a target polynucleotide sequence, comprising:

a computer processor; and a computer-readable storage medium coupled to said processor, the storage medium having instructions tangibly embodied thereon, the instructions when executed by said processor causing said processor to perform the operations of:

obtaining, using the processor, coverage values for each given position in a baseline or reference sample for the sequence coverage of said target polynucleotide using data generated from mate-pair mappings;

correcting, using the processor, the coverage values for each given position for sequence coverage bias, wherein correcting the coverage values for each given position in a baseline or reference sample comprises performing ploidy-aware baseline correction; and estimating, using a computer, a total copy number value and region-specific copy number value for each of a plurality of genomic regions based at least on the corrected coverage values for each given position in a baseline or reference sample.

* * * * *